United States Patent
Song et al.

(10) Patent No.: US 12,423,575 B2
(45) Date of Patent: Sep. 23, 2025

(54) METHOD AND APPARATUS FOR TRAINING RETROSYNTHESIS PREDICTION MODEL

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Youyoung Song, Suwon-si (KR); Seungwoo Seo, Suwon-si (KR); Jinwoo Shin, Daejeon (KR); Eunho Yang, Daejeon (KR); Sungju Hwang, Daejeon (KR)

(73) Assignees: SAMSUNG ELECTRONICS CO., LTD., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 1154 days.

(21) Appl. No.: 17/334,204

(22) Filed: May 28, 2021

(65) Prior Publication Data

US 2021/0374536 A1 Dec. 2, 2021

Related U.S. Application Data

(60) Provisional application No. 63/031,662, filed on May 29, 2020.

(30) Foreign Application Priority Data

Feb. 16, 2021 (KR) .................. 10-2021-0020694

(51) Int. Cl.
*G06N 3/08* (2023.01)
*G06F 16/901* (2019.01)
(Continued)

(52) U.S. Cl.
CPC .......... *G06N 3/08* (2013.01); *G06F 16/9024* (2019.01); *G06F 16/90344* (2019.01);
(Continued)

(58) Field of Classification Search
USPC ........................................................ 702/22
See application file for complete search history.

(56) References Cited

U.S. PATENT DOCUMENTS

2018/0341860 A1 11/2018 Shazeer et al.
2019/0370616 A1* 12/2019 Eser ...................... G06F 18/256
(Continued)

FOREIGN PATENT DOCUMENTS

| CN | 109863554 A | 6/2019 |
|----|-------------|--------|
| CN | 110913353 A | 3/2020 |

OTHER PUBLICATIONS

Bowen Liu et al., "Retrosynthetic Reaction Prediction Using Neural Sequence-to-Sequence Models", ACS Central Science, Sep. 5, 2017, vol. 3, pp. 1103-1113.
(Continued)

*Primary Examiner* — Paul D Lee
(74) *Attorney, Agent, or Firm* — Sughrue Mion, PLLC

(57) ABSTRACT

A method of training a retrosynthesis prediction model includes determining first attention information from first character string information of a product, based on first graph information of the product, encoding the first character string information, based on the determined first attention information, and determining second attention information from the first graph information and second graph information of a reactant. The method further includes decoding second character string information of the reactant, based on the determined second attention information, and training the retrosynthesis prediction model, based on the decoded second character string information.

15 Claims, 13 Drawing Sheets

(51) Int. Cl.
  *G06F 16/903* (2019.01)
  *G06F 18/214* (2023.01)
  *G06F 18/2415* (2023.01)
  *G16C 20/10* (2019.01)
  *G16C 20/70* (2019.01)

(52) U.S. Cl.
  CPC ...... *G06F 18/2148* (2023.01); *G06F 18/2415* (2023.01); *G16C 20/10* (2019.02); *G16C 20/70* (2019.02)

(56) References Cited

U.S. PATENT DOCUMENTS

| | | | | |
|---|---|---|---|---|
| 2021/0081717 A1* | 3/2021 | Creed | ............... | G06N 3/047 |
| 2021/0295955 A1* | 9/2021 | Lee | ............... | G06N 3/047 |
| 2021/0326389 A1* | 10/2021 | Sankar | ............... | G06F 18/214 |
| 2023/0169140 A1* | 6/2023 | Lee | ............... | G06V 10/426 |
| | | | | 706/31 |

OTHER PUBLICATIONS

Seung-Woo Seo et al., "GTA: Graph Truncated Attention for Retrosynthesis", Proceedings of the AAAI Conference on Artificial Intelligence, 2021, vol. 35 No. 1, pp. 531-539.

* cited by examiner

SMILES: c1cocc1      C=C      c1ccccc1

METHOD AND APPARATUS FOR TRAINING RETROSYNTHESIS PREDICTION MODEL

CROSS-REFERENCE TO RELATED APPLICATIONS

This application is based on and claims priority under 35 U.S.C. § 119 to Provisional Application No. 63/031,662, filed on May 29, 2020, in the U.S. Patent and Trademark Office, and Korean Patent Application No. 10-2021-0020694, filed on Feb. 16, 2021, in the Korean Intellectual Property Office, the disclosures of which are incorporated by reference herein in their entireties.

BACKGROUND

1. Field

The disclosure relates to a method and an apparatus for training a retrosynthesis prediction model.

2. Description of Related Art

A neural network refers to a computational architecture that models a biological brain. As neural network technology develops, various types of electronic systems may utilize neural networks to analyze input data and extract valid information.

There is a need to develop a technology that may accurately predict reactants from products by using neural networks.

SUMMARY

Provided are methods and apparatuses for training a retrosynthesis prediction model.

Additional aspects will be set forth in part in the description that follows and, in part, will be apparent from the description, or may be learned by practice of presented embodiments.

According to an aspect of an embodiment, there is provided a method of training a retrosynthesis prediction model, the method including determining first attention information from first character string information of a product, based on first graph information of the product, encoding the first character string information, based on the determined first attention information, and determining second attention information from the first graph information and second graph information of a reactant. The method further includes decoding second character string information of the reactant, based on the determined second attention information, and training the retrosynthesis prediction model, based on the decoded second character string information.

The encoding of the first character string information may include receiving the first character string information and the first graph information, generating a self-attention score matrix indicating a degree of relevance between tokens included in the received first character string information, applying a mask to the generated self-attention score matrix, based on the received first graph information, generating a self-attention matrix indicating a degree of attention of each of the tokens included in the first character string information as a probability, based on the self-attention score matrix to which the mask is applied, and outputting an encoded first output sequence, based on the generated self-attention matrix.

The generating of the self-attention matrix may include obtaining a query, a key, and a value from the received first character string information, and generating the self-attention matrix, based on the obtained query, key, and value.

The applying of the mask may include generating a first mask matrix, based on the received first graph information and a preset reference distance, determining elements to be paid attention when encoding the first character string information in the self-attention score matrix, based on generated the first mask matrix, and applying the mask to the generated self-attention score matrix, based on the determined elements.

The generating of the first mask matrix may include setting any one of nodes included in the received first graph information, as a reference node, expressing the reference node and adjacent nodes present at a distance separated by the preset reference distance from the reference node, among the nodes, as "1", and expressing remaining nodes, among the nodes, as "0".

The decoding of the second character string information may include receiving the second character string information and the second graph information, generating a cross-attention matrix indicating a degree of relevance between tokens included in the first character string information and tokens included in received the second character string information as a probability, applying a mask to the generated cross-attention matrix, based on atom-mapping information representing a relationship between atoms included in the product and atoms included in the reactant, and outputting a decoded second output sequence, based on the cross-attention matrix to which the mask is applied.

The generating of the cross-attention matrix may include obtaining a key and a value from the first character string information, obtaining a query from the received second character string information, and generating the cross-attention matrix, based on the obtained query, key, and value.

The applying of the mask may include obtaining the atom-mapping information, based on the first graph information and the received second graph information, determining whether the atoms included in the product correspond to the atoms included in the reactant, based on the obtained atom-mapping information, to generate a second mask matrix, determining elements to be paid attention when calculating an attention loss of the retrosynthesis prediction model in the generated cross-attention matrix, based on the generated second mask matrix, and applying the mask to the generated cross-attention matrix, based on the determined elements.

The generating of the second mask matrix may include setting any one of nodes included in the first graph information, as a reference node, expressing a node corresponding to the reference node, as "1", among nodes included in the second graph information, and representing remaining nodes, among the nodes, as "0".

The training of the retrosynthesis prediction model may include obtaining the attention loss of the retrosynthesis prediction model, from the cross-attention matrix to which the mask is applied, obtaining a cross entropy loss of the retrosynthesis prediction model, from the outputted decoded second output sequence, and training the retrosynthesis prediction model, based on the obtained attention loss and the obtained cross entropy loss.

The attention loss may be controllable by parameters.

The first character string information and the second character string information may be in a form of a simplified molecular-input line-entry system (SMILES) code type.

The first graph information and the second graph information may include at least one node and at least one edge, the at least one node includes information of atoms of the product or of the reactant, and the at least one edge includes information of a connection relationship of the atoms.

A non-transitory computer-readable recording medium may store a program for executing the method on a computer.

According to an aspect of an embodiment, there is provided an apparatus for predicting a reaction product by using a retrosynthesis prediction model, the apparatus including a memory in which at least one program is stored, and a processor that executes the at least one program, to determine first attention information from first character string information of a product, based on first graph information of the product, encode the first character string information, based on the determined first attention information, determine second attention information from the first graph information and second graph information of a reactant, decode second character string information of the reactant, based on the determined second attention information, and train the retrosynthesis prediction model, based on the decoded second character string information.

BRIEF DESCRIPTION OF THE DRAWINGS

The above and other aspects, features, and advantages of embodiments of the disclosure will be more apparent from the following description taken in conjunction with the accompanying drawings, in which.

DETAILED DESCRIPTION

Figure 1:
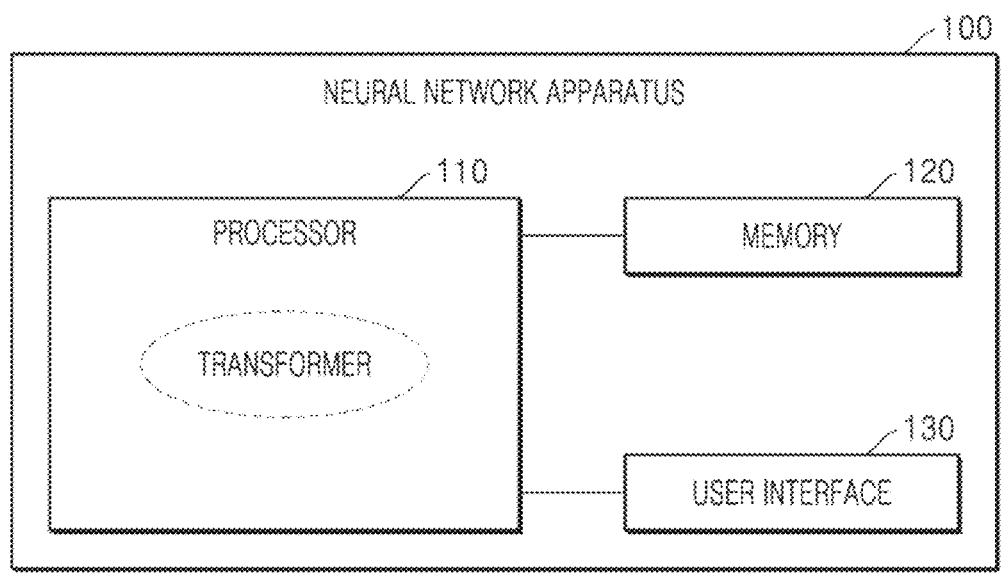
FIG. 1 is a block diagram of a neural network apparatus according to an embodiment.

Reference will now be made in detail to embodiments, examples of which are illustrated in the accompanying drawings, wherein like reference numerals refer to like elements throughout. In this regard, the exemplary embodiments may have different forms and may not be construed as being limited to the descriptions set forth herein. Accordingly, the exemplary embodiments are described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Phrases such as "in some embodiments" or "in one embodiment" appearing in various places in this specification are not necessarily all referring to the same embodiment.

Some embodiments of the disclosure may be represented by functional block configurations and various processing steps. Some or all of these functional blocks may be implemented with various numbers of hardware and/or software configurations that perform functions. For example, the functional blocks of the disclosure may be implemented by one or more microprocessors, or by circuit configurations for a predetermined function. Further, for example, the functional blocks of the disclosure may be implemented in various programming or scripting languages. The functional blocks may be implemented as an algorithm executed on one or more processors. In addition, the disclosure may employ the related art for electronic configuration, signal processing, and/or data processing. Terms, such as "mechanism", "element", "means" and "configuration" may be used widely and are not limited to mechanical and physical configurations.

Further, the connecting lines or connecting members between the components illustrated in the drawings are illustrative of functional connections and/or physical or circuit connections. In an actual device, connections between components may be represented by various functional connections, physical connections, or circuit connections that may be replaced or added.

In relation to the terms used in the specification, a structure, which is data used in a neural network system, may denote a structure at an atomic level of a material. The structure may be a structural formula based on a bond between an atom and an atom.

FIG. 1 is a block diagram of a neural network apparatus 100 according to an embodiment.

The neural network apparatus 100 may be implemented as various types of devices, such as a personal computer (PC), a server, a mobile device, and an embedded device, etc., and as examples, may correspond to a smartphone, a tablet device, an Augmented Reality (AR) device, an Internet of Things (IoT) device, an autonomous vehicle, robots, medical devices, etc. that perform voice recognition, image recognition, image classification, etc. using a neural network, but is not limited thereto. Furthermore, the neural network apparatus 100 may correspond to an exclusive hardware accelerator mounted in the above devices, and the neural network apparatus 100 may be a hardware accelerator, such as a neural processing unit (NPU), a Tensor Processing Unit (TPU), or a Neural Engine, which are exclusive modules for driving a neural network, but is not limited thereto.

Referring to FIG. 1, the neural network apparatus 100 includes a processor 110, a memory 120, and a user interface 130. In the neural network apparatus 100 shown in FIG. 1, only components related to the present embodiments are shown. Accordingly, it is obvious to those skilled in the art that the neural network apparatus 100 may further include other general-purpose components in addition to the components shown in FIG. 1.

The processor 110 controls overall functions for executing the neural network apparatus 100. For example, the processor 110 controls the neural network apparatus 100 by executing programs stored in the memory 120 in the neural network apparatus 100. The processor 110 may be implemented with a central processing unit (CPU), a graphics processing unit (GPU), an application processor (AP), etc. included in the neural network apparatus 100, but is not limited thereto.

The memory 120 is hardware configured to store various types of data processed by the neural network apparatus 100, for example, may store data processed and to be processed by the neural network apparatus 100. Also, the memory 120 may store applications, drivers, and the like to be driven by the neural network apparatus 100. The memory 120 may include random access memory (RAM), such as dynamic random access memory (DRAM) and static random access memory (SRAM), read-only memory (ROM), electrically erasable programmable read-only memory (EEPROM), a CD-ROM, Blu-ray or other optical disk storage, a hard disk drive (HDD), a solid state drive (SSD), or flash memory.

The processor 110 may train a retrosynthesis prediction model through a test data set, and predict at least one combination of reactants from a target product based on the trained retrosynthesis prediction model. The retrosynthesis prediction may denote a prediction of a combination of reactant molecules for synthesizing a target product by searching for an inverse reaction pathway of the target product.

The retrosynthesis prediction model may be implemented by using a transformer model. As the neural network apparatus 100 uses the transformer model, parallel processing and rapid computation of data may be performed.

The processor 110 may train a transformer model by using a test data set.

The test data set may include test products and a test reactant combination corresponding to each of the test products. For example, any one of the test products may be benzene, and a combination of test reactants corresponding to benzene may be furan and ethylene.

According to an embodiment, the test data set may further include a predicted yield of test products according to an experimental condition and reaction modes of each of the test reactant combinations.

The experimental condition may refer to various conditions set to conduct an experiment for generating a product by using reactants. For example, the experimental conditions may include any one or any combination of a catalyst, a base, a solvent, a reagent, a temperature, and a reaction time.

The reaction mode may refer to a chemical reaction method for producing a product by using reactant combinations.

The processor 110 may receive test products and a test reactant combination corresponding to each of the test products to train a retrosynthesis prediction model.

The processor 110 may receive a chemical structure of a test product in a one-dimensional character string format and a two-dimensional graph format. In addition, the processor 110 may receive a chemical structure of a test reactant in a one-dimensional character string format and a two-dimensional graph format.

The processor 110 may encode first character string information of a test product in a vector format.

The processor 110 may determine information to be paid attention from the first character string information based on the first graph information of the test product, and encode the first character string information based on the determination result. Information to be paid attention in the first character string information may be referred to as first attention information. The first attention information may be information about neighbor atoms that are adjacent to an encoding target atom. In other words, the processor 110 may obtain information about the neighboring atoms of the encoding target atom from the first graph information of the test product, and further pay attention to a relationship between the encoding target atom and the neighboring atoms, and thus, may encode the encoding target atom.

As the processor 110 specifies information related to input information (e.g., a token) from the entire character string information and encodes the input information by paying attention to the specified information, information loss (vanishing) caused by encoding all character string information into a fixed-length vector may be reduced. In addition, as the processor 110 encodes an encoding target atom by further paying attention to the relationship between the encoding target atoms that are highly chemically related to the encoding target atom, efficient training and rapid training of the retrosynthesis prediction model may be performed and the accuracy of the retrosynthesis prediction model may be significantly improved.

The processor 110 may output the encoded first character string information as a first output sequence.

The processor 110 may determine information to be paid attention from first graph information of a test product and second graph information of a test reactant, and decode second character string information of the reactant based on the determination result. Information to be paid attention from the first graph information and the second graph information may be referred to as second attention information. The relationship between the test product and the test reactant may be expressed as a cross-attention matrix, and an ideal cross-attention matrix may catch atom-mapping information representing a relationship between atoms included in a product and atoms included in a reactant. Accordingly, information to be paid attention in the first graph information and the second graph information for training of the retrosynthesis prediction model may be atom-mapping information. In other words, the processor 110 may obtain atom-mapping information from the first graph information and the second graph information, and decode a decoding target atom by further paying attention to the atom-mapping information.

When the processor 110 predicts output information (e.g., a token), as the processor 110 specifies a highly related part (e.g., a token) in the input character string information, and decodes input information by paying attention to the specified information, information loss (vanishing) according to the increase in the length of the input character string may be reduced.

In addition, as the processor 110 decodes a decoding target atom by further paying attention to the atom-mapping information to train the retrosynthesis prediction model, efficient training and rapid training of the retrosynthesis prediction model may be performed, and the accuracy of the retrosynthesis prediction model may be significantly increased.

The processor 110 may train the retrosynthesis prediction model based on a result of decoding the second character string information. That the processor 110 trains the retrosynthesis prediction model may mean the training of hidden states of the encoder and the decoder so that the cross-attention matrix catches the atom-mapping information. In addition, that the processor 110 trains the retrosynthesis prediction model may mean the training of information on an edge representing a relationship between a node and a node in the graph information of each test product and test reactant. Further, that the processor 110 trains the retrosynthesis prediction model may mean that the accuracy of the prediction result of the neural network apparatus 100 is increased. According to an embodiment, that the processor 110 trains a retrosynthesis prediction model may mean the training of atom-mapping information indicating a relationship between an atom included in a product and an atom included in a reactant.

The processor 110 may predict at least one candidate reactant combination from an input product based on the trained retrosynthesis prediction model. Because the retrosynthesis prediction model is implemented by using a transformer model, the processor 110 may predict a candidate reactant combination from an input product by using the transformer model.

The user interface 130 may be via which feedback of an experiment result may be input. For example, the user interface 130 may include a key pad, a dome switch, a touch pad (a contact capacitive method, a pressure resistive film method, an infrared sensing method, a surface ultrasonic conduction method, an integral tension measurement method, a piezoelectric effect method, etc.), a jog wheel, a jog switch, and the like, but is not limited thereto. The processor 110 may update the transformer model by receiving feedback of the experimental results.

In the following description of the disclosure, a method of training a retrosynthesis prediction model will be described in detail. The methods described below may be performed by the processor 110, the memory 120, and the user interface 130 of the neural network apparatus 100. In addition, for convenience of description, hereinafter, a product refers to a test product, and a reactant refers to a test reactant.

Figure 2:
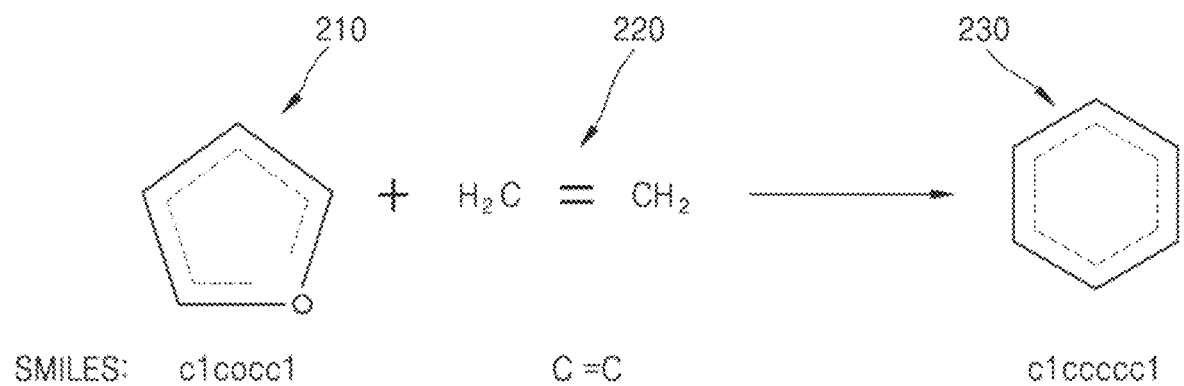
FIG. 2 is a diagram of character string information according to an embodiment.

FIG. 2 is a diagram of character string information according to an embodiment.

Referring to FIG. 2, the chemical structures of products and reactants may be input to the neural network apparatus 100 in a one-dimensional character string format. The chemical structure may be a structural formula based on a bond between atoms. In one embodiment, the processor 110 may receive a chemical structure of a product and a reactant in the form of a Simplified Molecular-Input Line-Entry System (SMILES).

The SMILES notation is not unique and varies depending on the selection of a central atom or the beginning of a sequence, and thus, a standardized algorithm may be used. The SMILES notation of the disclosure separates each atomic token (e.g., B, C, N, or O) and a non-atomic token. The non-atomic token may include interatomic bonds (e.g., -, =, or #), parentheses, a number of cyclic structures with whitespaces, and the like.

For example, when furan 210 is combined with ethylene 220 to produce benzene 230, the SMILES of furan 210, ethylene 220, and benzene 230 may be respectively expressed as c1cocc1, c=c, and c1ccccc1.

In FIG. 2, although only the SMILES notation is shown, according to an embodiment, the processor 110 may be able to receive an input of a chemical structure of a product and a reactant in a smiles arbitrary target specification (SMARTS) format or an international chemical identifier (InChi) format.

Figure 3:
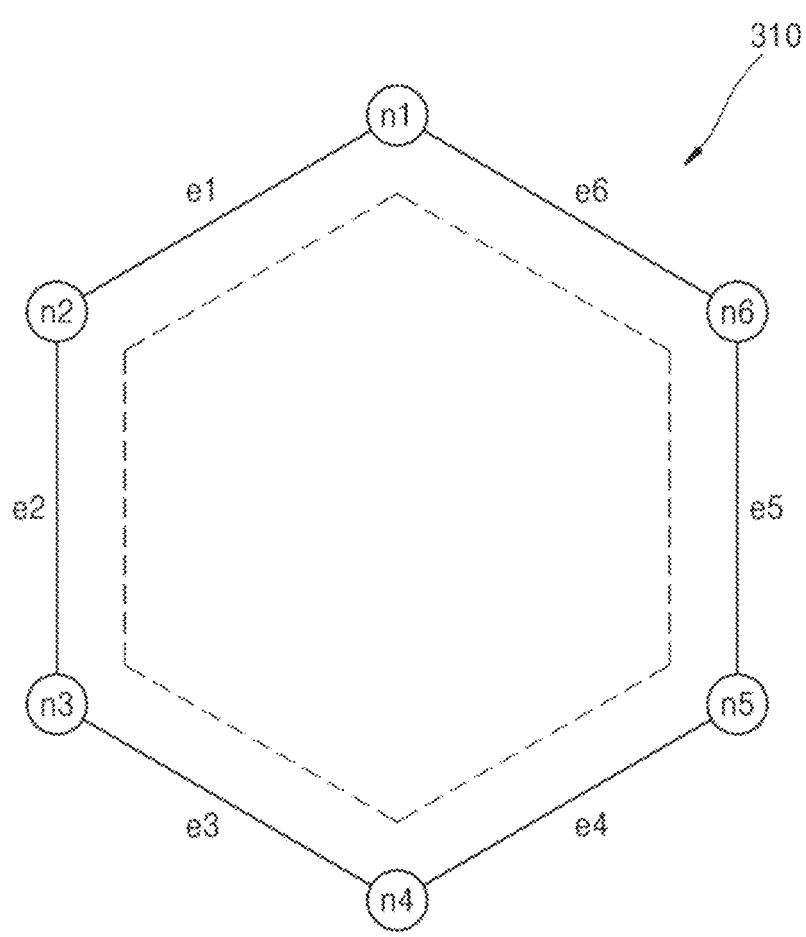
FIG. 3 is a diagram of graph information according to an embodiment.

FIG. 3 is a diagram of graph information 310 according to an embodiment.

Referring to FIG. 3, a chemical structure of a product and a reactant may be input to the neural network apparatus 100 in the form of a two-dimensional graph.

Graph information may include a node and an edge. A node may include information about an atom of a product and a reactant, and an edge may include information about a connection relationship between atoms.

The transformer model encodes and decodes character string information, but it may also be reinterpreted as a graph neural network. In one embodiment, tokens of a source sequence and a target sequence input to the transformer model may correspond to nodes. In addition, the attention of the transformer model may correspond to the edge. For example, the graph information 310 of benzene 230 may include first to sixth nodes n1 to n6. Also, the graph information 310 may include first to sixth edges e1 to e6 indicating a connection relationship between the nodes. The edge value may not be known initially, but may be identified by training a transformer model.

Figure 4:
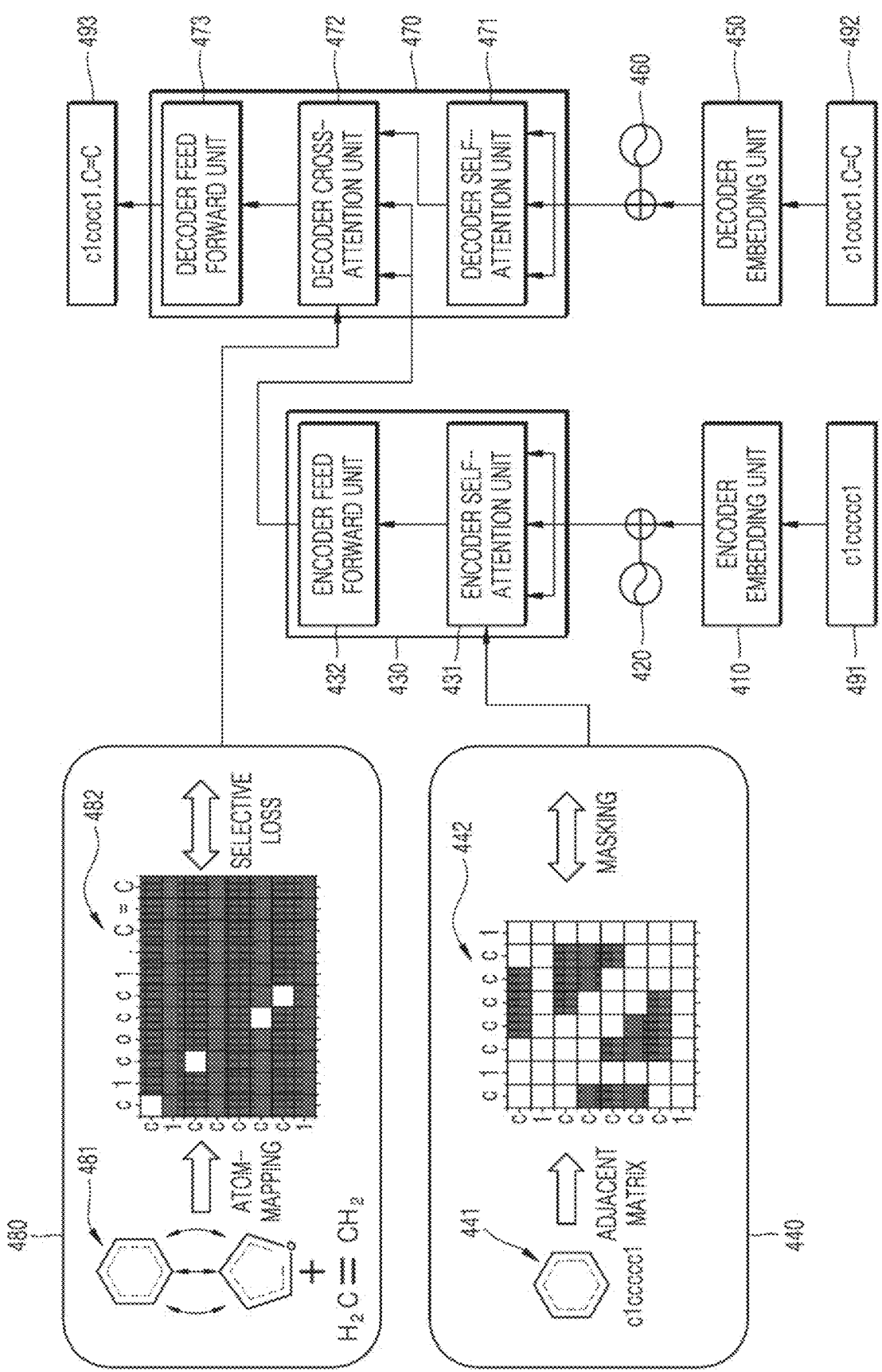
FIG. 4 is a diagram for describing a method of training a retrosynthesis prediction model, according to an embodiment.

FIG. 4 is a diagram for describing a method of training a retrosynthesis prediction model, according to an embodiment.

Referring to FIG. 4, the processor 110 may train the retrosynthesis prediction model through a test data set, and predict at least one combination of reactants from a target product based on the trained retrosynthesis prediction model. To this end, the processor 110 may include an encoder embedding unit 410, a first position encoding unit 420, an encoder 430, a first mask matrix generator 440, a decoder embedding unit 450, a second position encoding unit 460, a decoder 470, and a second mask matrix generator 480. In FIG. 4, the encoder embedding unit 410, the first position encoding unit 420, the encoder 430, the first mask matrix generator 440, the decoder embedding unit 450, the second position encoding unit 460, the decoder 470, and the second mask matrix generator 480 are shown as any one unit included in the processor 110, but the encoder embedding unit 410, the first position encoding unit 420, the encoder 430, the first mask matrix generator 440, the decoder embedding unit 450, the second position encoding unit 460, the decoder 470, and the second mask matrix generator 480 may also denote a layer included in the transformer model of the processor 110. In addition, the residual connection sublayer and the normalization sublayer may be individually applied to all lower layers.

The encoder embedding unit 410 may embed input data in character units. In this case, the input data may denote first character string information 491 of the product. In other words, the encoder embedding unit 410 may map the first character string information 491 in a character string format to a vector of a preset dimension. For example, the preset dimension may be 512 dimension, but is not limited thereto.

The first position encoding unit 420 may perform positional encoding to identify the position of each character included in the first character string information 491. For example, the first position encoding unit 420 may position-encode the first character string information 491 by using a sinusoids of a different frequency. The first position encoding unit 420 may combine the position information with the embedded first character string information 491 and provide the combined result to the encoder 430.

The encoder 430 may include an encoder self-attention unit 431 and an encoder feed forward unit 432. In FIG. 4, the encoder 430 is illustrated as one unit, but N encoders may be stacked. In addition, in FIG. 4, the encoder self-attention unit 431 and the encoder feed forward unit 432 are represented as one unit in the encoder 430, but the encoder self-attention unit 431 and the encoder feed forward unit 432 may denote sub-layers included in the encoder layer, respectively.

The encoder self-attention unit 431 may specify information to be paid self-attention in the first character string information 491 when encoding the first character string information 491. To this end, the encoder self-attention unit 431 may generate a self-attention score matrix. A score indicating a degree of relevance between character strings included in the first character string information 491 may be mapped to the self-attention score matrix. The encoder self-attention unit 431 may generate a self-attention matrix representing element values of the self-attention score matrix as a probability by using a soft max function.

When encoding an input character string based on the self-attention matrix, the encoder 430 may specify elements to be paid self-attention in the first character string information 491. The encoder self-attention unit 431 may be configured as a multi-head to generate a plurality of self-attention matrices.

On the other hand, the encoder self-attention unit 431 may not control a space expressing a degree of relevance between tokens included in the first character string information 491, but the space for expressing a degree of relation may be limited by using a graph structure that may be applied to self-attention and cross-attention, which will be described later.

The processor 110 may determine information to be paid attention when encoding the first character string information 491 in the self-attention score matrix and/or the self-attention matrix based on first graph information 441 for efficiency, speed, and accuracy of training. Information to be paid attention in the self-attention score matrix and/or the self-attention matrix may be first attention information. To this end, the first mask matrix generator 440 may generate a first mask matrix 442 that masks unnecessary elements in the self-attention score matrix and/or the self-attention matrix.

The first mask matrix generator 440 may generate the first mask matrix 442 based on the first graph information 441 of the product and a preset reference distance.

The first mask matrix generator 440 may generate a first pre-mask matrix by setting tokens included in the first character string information 491 as rows and columns. Also, the first mask matrix generator 440 may determine neighboring nodes adjacent to each other from the first graph information 441 based on a preset reference distance. Also, the first mask matrix generator 440 may generate the first mask matrix 442 based on the determined neighboring nodes. For example, the first mask matrix generator 440 may generate the first mask matrix 442 by allocating information about nodes for calculating a self-attention matrix to the first pre-mask matrix, and by assigning '1' to neighboring nodes adjacent to the reference node and '0' to the remaining nodes. The generation of the first mask matrix 442 by the first mask matrix generator 440 based on neighboring nodes of the reference node is to train the retrosynthesis prediction model by paying further attention to the neighboring nodes that have a large chemical relationship with the reference node.

The first mask matrix generator 440 may provide the first mask matrix 442 to the encoder self-attention unit 431.

The encoder self-attention unit 431 may determine an element to be paid attention when encoding the first character string information 491 in the self-attention matrix based on the first mask matrix 442. Also, the encoder self-attention unit 431 may output a self-attention matrix to which a mask is applied based on the determination result.

The self-attention matrix to which a mask is applied may be provided to the encoder feed forward unit 432.

The encoder feed forward unit 432 may include a feed-forward neural network. An input sequence converted may be outputted by the feed-forward neural network. The input sequence converted may be provided to the decoder 470.

The decoder embedding unit 450 may embed input data in character units. At this point, input data may denote second character string information 492 of a reactant. In other words, the decoder embedding unit 450 may map the second character string information 492 in a character string format to a vector of a preset dimension. For example, the preset dimension may be 512 dimensions, but is not limited thereto.

The second position encoding unit 460 may perform positional encoding to identify the position of each character included in the second character string information 492. For example, the second position encoding unit 460 may position-encode the second character string information 492 by using a sinusoids of a varying frequency. The second position encoding unit 460 may combine the position information with the embedded second character string information 492 and provide it to the decoder 470.

The decoder 470 may include a decoder self-attention unit 471, a decoder cross-attention unit 472, and a decoder feed forward unit 473. Like the encoder 430, the decoder 470 is illustrated as one unit, but may be a stack type of N decoders. In addition, the decoder self-attention unit 471, the decoder cross-attention unit 472, and the decoder feed forward unit 473 are displayed as one unit, but the decoder self-attention unit 471, the decoder cross-attention unit 472, and the decoder feed forward unit 473 each may denote a sub-layer included in a decoder layer.

The decoder self-attention unit 471 may perform an operation similar to that of the encoder self-attention unit 431. In other words, when decoding the second character string information 492, the decoder self-attention unit 471 specifies information to be paid self-attention from the second character string information 492, and generates a self-attention matrix based on the specified information. In addition, the decoder self-attention unit 471 may be configured as a multi-head to generate a plurality of self-attention matrices. To distinguish a self-attention matrix generated by the decoder self-attention unit 471 from a self-attention matrix generated by the encoder self-attention unit 431, the self-attention matrix generated by the encoder self-attention unit 431 may be referred to as a first self-attention matrix, and the self-attention matrix generated by the decoder self-attention unit 471 may be referred to as a second self-attention matrix.

A difference between the decoder self-attention unit 471 and the encoder self-attention unit 431 is whether or not a mask is applied. The decoder self-attention unit 471 does not mask the self-attention matrix by using the first mask matrix 442 described with the encoder self-attention unit 431. However, the decoder self-attention unit 471 may use a mask to prevent a current output position from being used as information on the next output position.

The decoder cross-attention unit 472 may specify information to be paid cross-attention in the first character string information 491 when decoding the second character string information 492. To this end, the decoder cross-attention unit 472 may generate a cross-attention score matrix indicating a degree of relevance between the second character string information 492 and the first character string information 491. A score indicating a degree of relevance between character strings included in the first character string information 491 and character strings included in the second character string information 492 may be mapped to the cross-attention score matrix. The decoder cross-attention unit 472 may generate a cross-attention matrix representing values of the elements of the cross-attention score matrix as a probability by using a soft max function. When decoding the input character string based on the cross-attention matrix, the decoder 470 may specify elements to be paid cross-attention from the first character string information 491.

The processor 110 may determine information to be paid attention when calculating an attention loss in the cross-attention matrix based on first graph information 441 and second graph information 481 for efficiency, speed, and accuracy of training. Information to be paid attention in the cross-attention matrix may be second attention information. To this end, the second mask matrix generator 480 may generate a second mask matrix 482 that masks unnecessary elements in the cross-attention matrix. Roles of the first mask matrix 442 and the second mask matrix 482 may be different from each other. Unlike the first mask matrix 442, the second mask matrix 482 may be a matrix for masking unnecessary elements when calculating the attention loss of the retrosynthesis prediction model.

The second mask matrix generator 480 may obtain atom-mapping information indicating a correspondence relationship between atoms included in the product and atoms included in the reactant based on the first graph information 441 and the second graph information 481, and generate the second mask matrix 482 based on the atom-mapping information.

The second mask matrix generator 480 may generate a second pre-mask matrix by setting the second character string information 492 as a row and setting the first character string information 491 as a column. Also, the second mask matrix generator 480 may obtain atom-mapping information from the first graph information 441 and the second graph information 481. When a maximum common substructure (MCS) technique is used to determine the similarity between the first graph information 441 and the second graph information 481, a non-deterministic polynomial time (NP)-hard problem may occur. Therefore, the atom-mapping information of the disclosure does not require accurate atom-mapping information to determine the similarity between the first graph information 441 and the second graph information 481, and may be set by using a flexible maximum common substructure (FMCS) technique that utilizes only a pair of pieces of information. The FMCS may be an FMCS algorithm implemented in RDkit. As the second mask matrix generator 480 uses atom-mapping using only a pair of pieces of information rather than accurate atom-mapping information, computing cost may be reduced.

The second mask matrix generator 480 may generate a second mask matrix 482 based on the obtained atom-mapping information. For example, the second mask matrix generator 480 may generate the second mask matrix 482 by allocating information about nodes for computing an attention loss to the second pre-mask matrix, and by assigning '1' to nodes corresponding to each other and '0' to the remaining nodes.

The second mask matrix generator 480 may provide the second mask matrix 482 to the decoder cross-attention unit 472.

The decoder cross-attention unit 472 may determine an element to be paid attention when computing an attention loss of the retrosynthesis prediction model in the cross-attention matrix based on the second mask matrix 482. Also, the decoder cross-attention unit 472 may output a cross-attention matrix to which a mask is applied based on the determination result. A cross-attention matrix to which a mask is applied may be provided to the decoder feed forward unit 473.

The decoder feed forward unit 473 may perform an operation similar to that of the encoder feed forward unit 432. In other words, the decoder feed forward unit 473 includes a feed-forward neural network, and an input sequence may be transformed by a feed-forward neural network. The decoder feed forward unit 473 may output a converted input sequence as output reactant information 493.

The processor 110 may obtain an attention loss of the retrosynthesis prediction model from a cross-attention matrix to which a mask is applied. Also, the processor 110 may obtain a cross entropy loss of the retrosynthesis prediction model from the output reactant information 493.

The processor 110 may train a retrosynthesis prediction model based on the attention loss and the cross entropy loss. For example, the processor 110 may train the retrosynthesis prediction model so that the sum of the attention loss and the cross entropy loss decreases.

Figure 5:
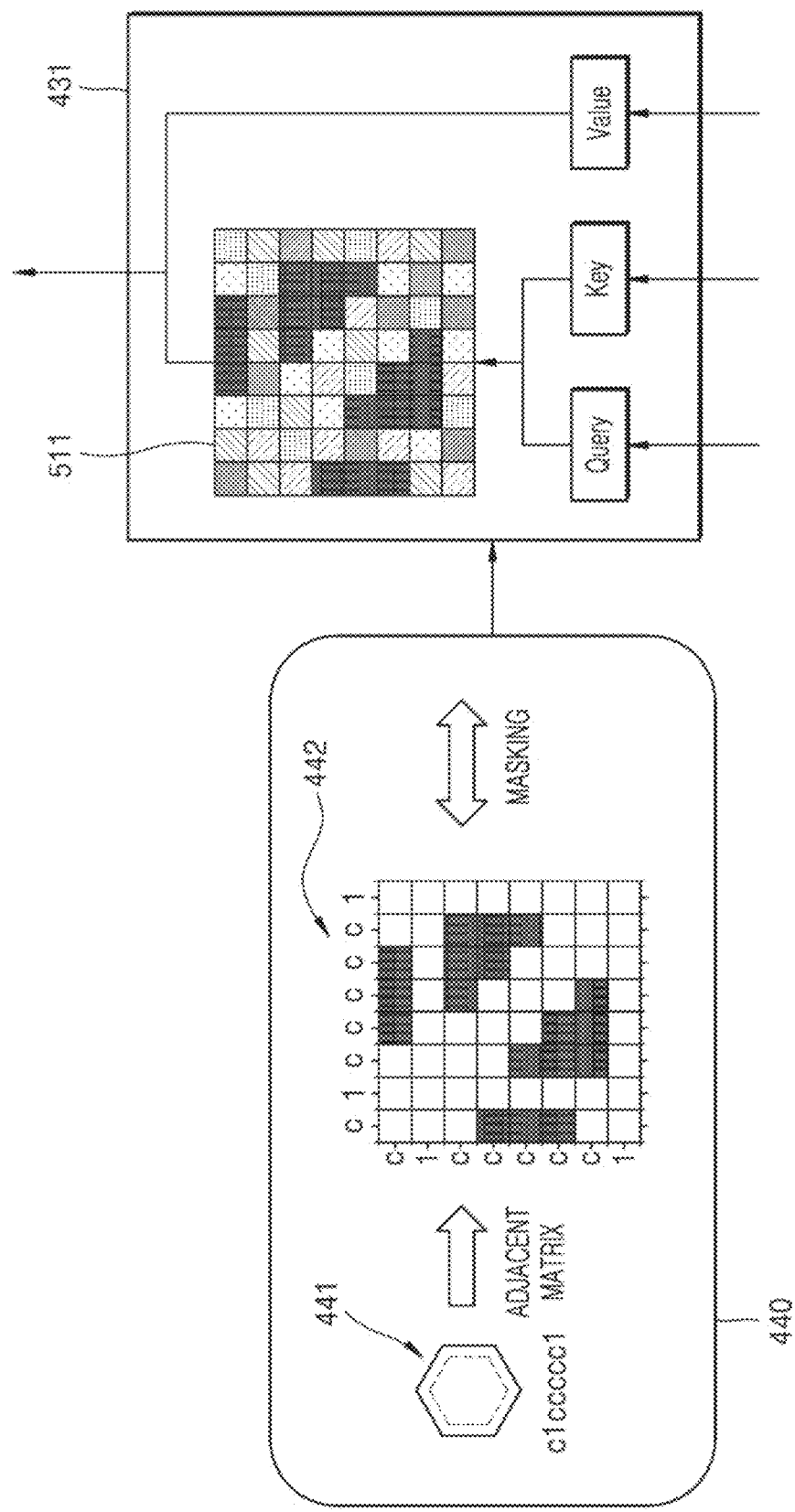
FIG. 5 is a diagram for describing an encoding method according to an embodiment.
Figure 6:
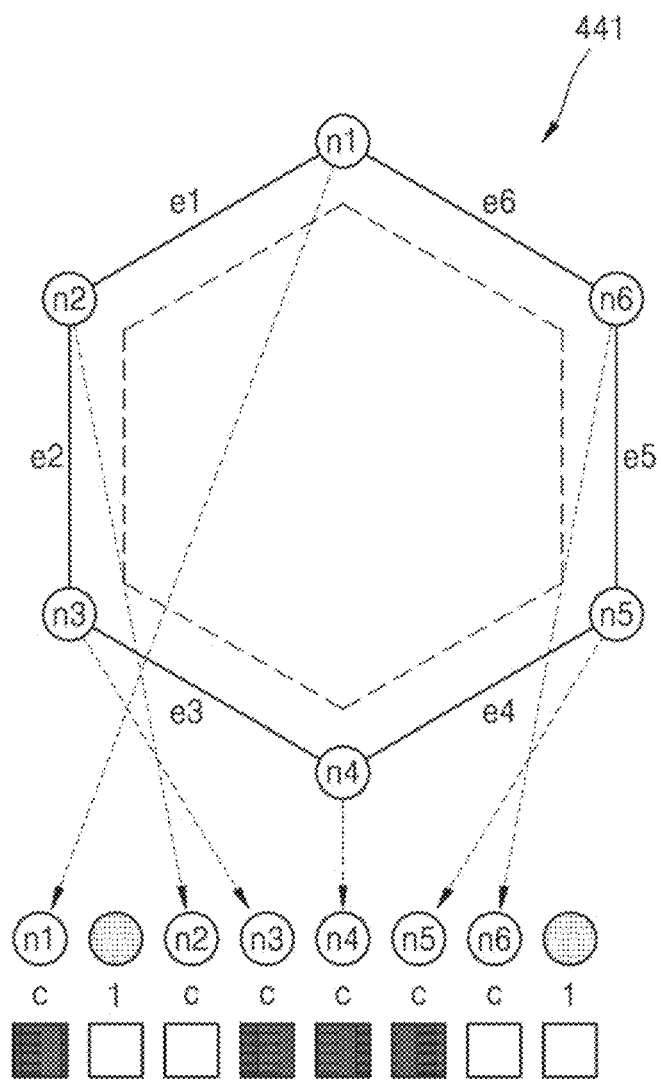
FIG. 6 is a diagram for describing a method of generating a first mask matrix, according to an embodiment.
Figure 7:
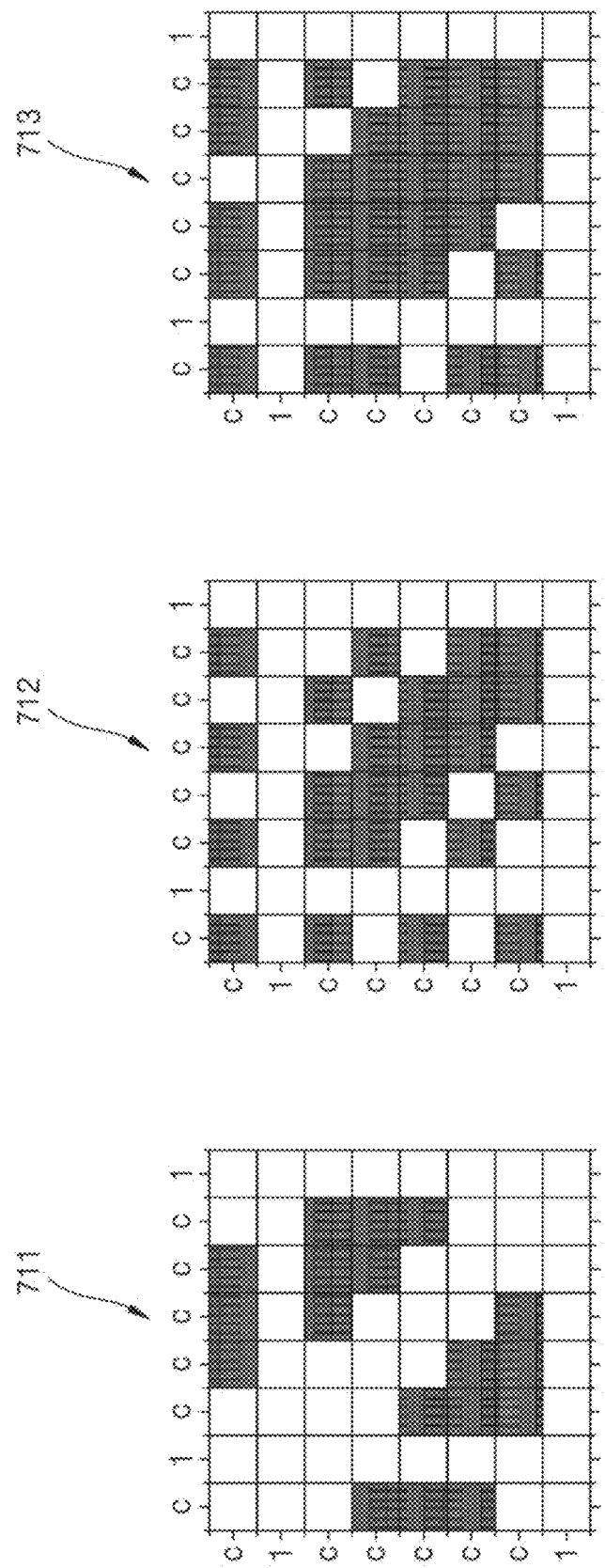
FIG. 7 is a reference diagram for describing a method of generating a first mask matrix, according to an embodiment.
Figure 8:
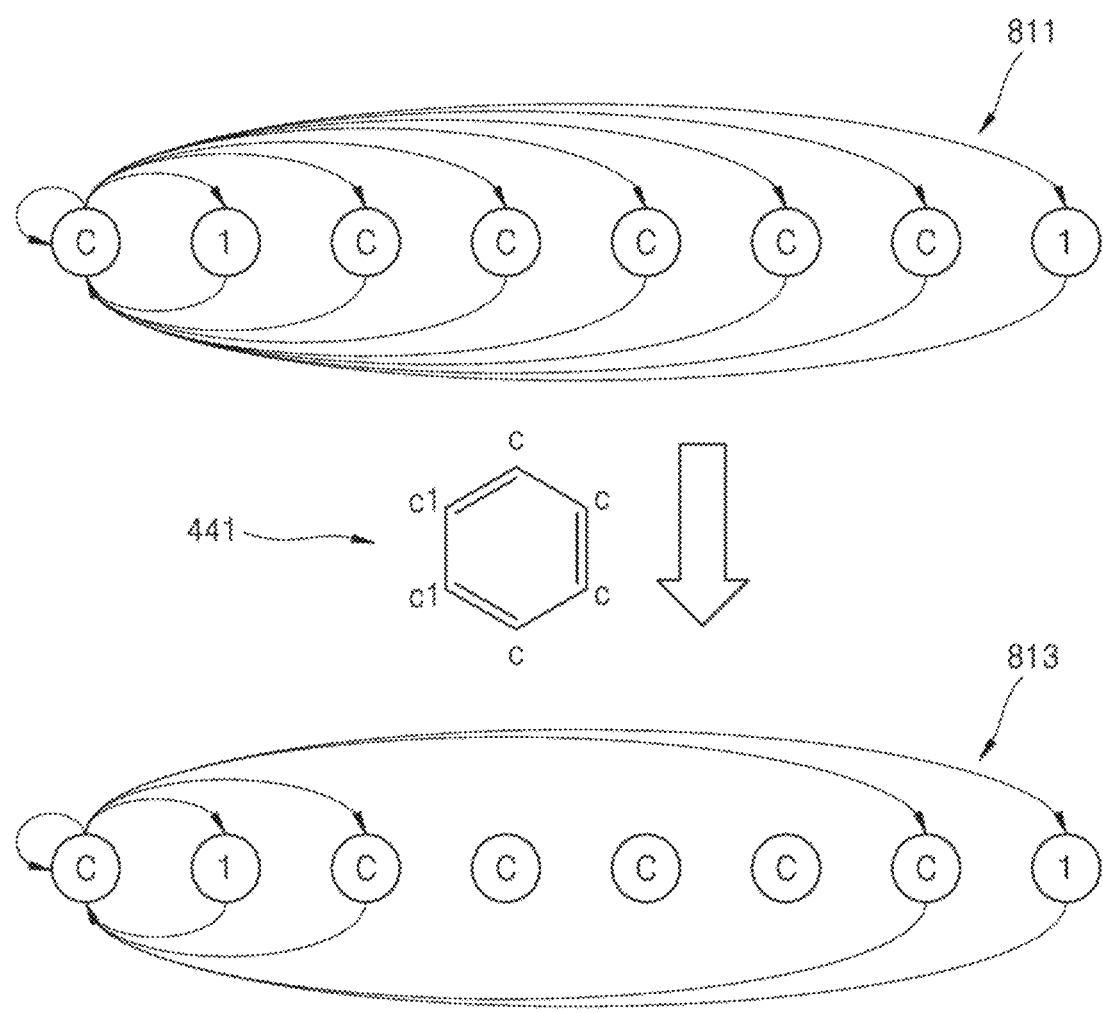
FIG. 8 is a diagram for describing an effect of a first mask matrix, according to an embodiment.

FIG. 5 is a diagram for describing an encoding method according to an embodiment, FIG. 6 is a diagram for describing a method of generating a first mask matrix, according to an embodiment, FIG. 7 is a reference diagram for describing a method of generating a first mask matrix, according to an embodiment, and FIG. 8 is a diagram for describing an effect of a first mask matrix, according to an embodiment.

Referring to FIG. 5, the encoder self-attention unit 431 may obtain query, key, and value information from the first character string information 491. The encoder self-attention unit 431 may convert an input vector sequence having a first dimension into a query vector, a key vector, and a value vector having a second dimension less than the first dimension. The input vector sequence may denote a vector sequence of the first character string information 491 converted by the encoder embedding unit 410 and the first position encoding unit 420. Dimensional conversion may be performed by multiplying each vector by a weight matrix. The weight matrix may be updated by training. For example, the first dimension may be 512 and the second dimension may be 64, but is not limited thereto.

The encoder self-attention unit 431 may generate a self-attention score matrix 511 based on a query and a key. The encoder self-attention unit 431 may determine a degree of relationship of all keys for each query, and display the determination result in the self-attention score matrix 511. The self-attention score matrix 511 may include information on a score indicating a degree of relationship between a query and a key. In an embodiment, the self-attention score matrix 511 may be derived by a scaled dot product attention operation as shown in Equation 1.

$$S = \frac{QK^T}{\sqrt{d_k}}$$ [Equation 1]

$$S = \frac{QK^T}{\sqrt{d_k}}$$

In Equation 1, S denotes a self-attention score matrix 511, Q denotes a query vector, K denotes a key vector, T denotes a transpose matrix, and $d_k$ denotes a dimension of a key vector.

The encoder self-attention unit 431 may receive the first mask matrix 442 from the first mask matrix generator 440.

The first mask matrix generator 440 may generate the first mask matrix 442 that masks unnecessary elements from the self-attention score matrix 511.

To train a retrosynthesis prediction model by paying attention to neighboring nodes that are highly chemically related to the encoding target node, the first mask matrix generator 440 may determine neighbor nodes adjacent to a target node from the first graph information 441 based on a preset reference distance, and may generate the first mask matrix 442 based on the determination result. In this case, the distance may denote a geodesic distance on a graph. Also, the distance may denote a hop neighbor on the graph.

The first mask matrix generator 440 may set any one node from among nodes included in the first graph information 441 as a reference node. Also, adjacent nodes present at a distance apart from a reference node by a reference distance may be expressed as "1", and the remaining nodes may be expressed as "0". According to an embodiment, the first mask matrix generator 440 may express a reference node and adjacent nodes that are present at a distance apart by a reference distance from the reference node as "1" and the remaining nodes as "0".

FIG. 6 illustrates a method, performed by the first mask matrix generator 440, of generating the first mask matrix 442 when the reference node is n1 and the reference distance is 1.

Referring to FIG. 6, the first mask matrix generator 440 may set any one of the nodes n1 to n6 included in the first graph information 441 as the reference node n1. Also, the first mask matrix generator 440 may determine neighboring nodes n2 and n6 present at a distance apart from the first reference node n1 by a reference distance. The first mask matrix generator 440 may allocate information about the reference node n1 and the neighboring nodes n2 and n6 adjacent to the reference node n1 to the first pre-mask matrix. In an embodiment, the first mask matrix generator 440 may allocate "1" to the reference node n1 and neighboring nodes n2 and n6, and "0" to the remaining nodes. FIG. 6 illustrates an example in which "1" is allocated to the neighboring nodes n2 and n6, but according to an embodiment, the first mask matrix generator 440 may allocate "1" to the reference node n1 and the neighboring nodes n2 and n6 adjacent to the reference node n1 and "0" to the remaining nodes.

On the other hand, because the first character string information 491 further includes non-atomic tokens, such as the number of cyclic structures having interatomic bonds (e.g., -, =, or #), parentheses, and whitespace in addition to atomic tokens, tokens of the first character string information 491 and nodes of the first graph information 441 do not coincide with each other. Because these non-atomic tokens may become clear in an entire context of character string information, a wider range of information may be required. Accordingly, the first mask matrix generator 440 may not mask nodes corresponding to non-atomic tokens. In other words, the first mask matrix generator 440 may allocate "1" to nodes corresponding to non-atomic tokens. Because non-atomic tokens exchange attention with all other tokens regardless of the graph structure, the accuracy of the retrosynthesis prediction model may be improved.

The first mask matrix generator 440 may change a reference node and determine neighboring nodes adjacent to the changed reference node. Also, the first mask matrix generator 440 may generate the first mask matrix 442 based on a result of determination.

When information on a reference distance is stored distance matrix $D=(d_{ij})$, elements included in the first mask matrix 442 may be determined by Equation 2 below.

$$m_{ij} = \begin{cases} 1 & \text{if } d_{ij} = d_h \\ 0 & \text{otherwise} \end{cases} \quad \text{[Equation 2]}$$

$$m_{ij} = \begin{cases} 1 & \text{if } d_{ij} = d_h \\ 0 & \text{otherwise} \end{cases}$$

In Equation 2, $m_{ij}$ denotes an element value included in the first mask matrix 442, and i and j denote atomic tokens. $d_h$ is a reference distance set to the $h^{th}$ head, and the first mask matrix generator 440 may set a different reference distance for each head. In other words, the first mask matrix generator 440 may generate a plurality of first mask matrices having different reference distances from each other and provide them to each head included in the encoder self-attention unit 431.

FIG. 7 shows an example of a mask matrix according to a reference distance. FIG. 7 shows a first mask matrix 711 when the reference distance is 1, a first mask matrix 712 when the reference distance is 2, and a first mask matrix 713 when the reference distance is 3.

Referring to FIG. 7, the first mask matrix generator 440 may set a reference distance of the first mask matrix 711 provided to the first head to 1, a reference distance of the first mask matrix 712 provided to the second head to 2, and a reference distance of the first mask matrix 713 provided to the third head to 3. As the first mask matrix generator 440 sets the reference distances of the first mask matrices provided to each head to be different from each other, training of the retrosynthesis prediction model may be enhanced.

Referring to FIG. 5, the first mask matrix generator 440 may provide the first mask matrix 442 to the encoder self-attention unit 431.

The encoder self-attention unit 431 may mask the self-attention score matrix 511 based on the first mask matrix 442.

When the self-attention score matrix 511 is $S=(s_{ij})$ and the first mask matrix 442 is $M=(M_{ij})$, the self-attention score matrix 511 to which the mask is applied is expressed as Equation 3 below.

$$[\text{Masking}(S, M)]_{ij} = \begin{cases} s_{ij} & \text{if } m_{ij} = 1 \\ -\infty & \text{if } m_{ij} = 0 \end{cases} \quad \text{[Equation 3]}$$

$$[\text{Masking}(S, M)]_{ij} = \begin{cases} s_{ij} & \text{if } m_{ij} = 1 \\ -\infty & \text{if } m_{ij} = 0 \end{cases}$$

As in Equation 3, when an element of the first mask matrix 442 is 1 (i.e., $m_{ij}=1$), the element of the self-attention score matrix 511 may be output as it is, and when the element of the first mask matrix 442 is 0 (i.e., $m_{ij}=0$), "$-\infty$" may be output.

The encoder self-attention unit 431 calculates the attention distribution of the self-attention score matrix 511 to which a mask is applied by using a softmax function, and may generate an attention value by weighted sum of the calculated result and each value. Attention values may be expressed as a self-attention matrix. The score of the self-attention score matrix 511 may be expressed as a probability by a soft max function. Because the self-attention matrix includes context information of a sequence, the self-attention matrix may be referred to as a context vector. In other words, the encoder self-attention unit 431 may output a self-attention matrix to which a mask is applied by Equation 4 below.

$$\text{Attention}(Q,K,V)=\text{softmax}(\text{Masking}(S,M))V$$

$$\text{Attention}(Q,K,V)=\text{softmax}(\text{Masking}(S,M))V \quad \text{[Equation 4]}$$

As the encoder self-attention unit 431 outputs a self-attention matrix from which unnecessary elements are removed, training efficiency, speed, and accuracy may be improved.

In FIG. 8, a graph 811 for describing an operation method of the processor 110 when an encoder self-attention is performed without applying the first mask matrix 442 and a graph 813 for explaining an operation method of the processor 110 when an encoder self-attention is performed by applying the first mask matrix 442 are shown.

Referring to FIG. 8, in training of the retrosynthesis prediction model, the processor 110 removes unnecessary elements and focuses more on the relationship between neighboring nodes that are highly chemically related, and thus, without introducing an additional parameter, the efficiency, speed, and accuracy of the training may be increased.

Figure 9:
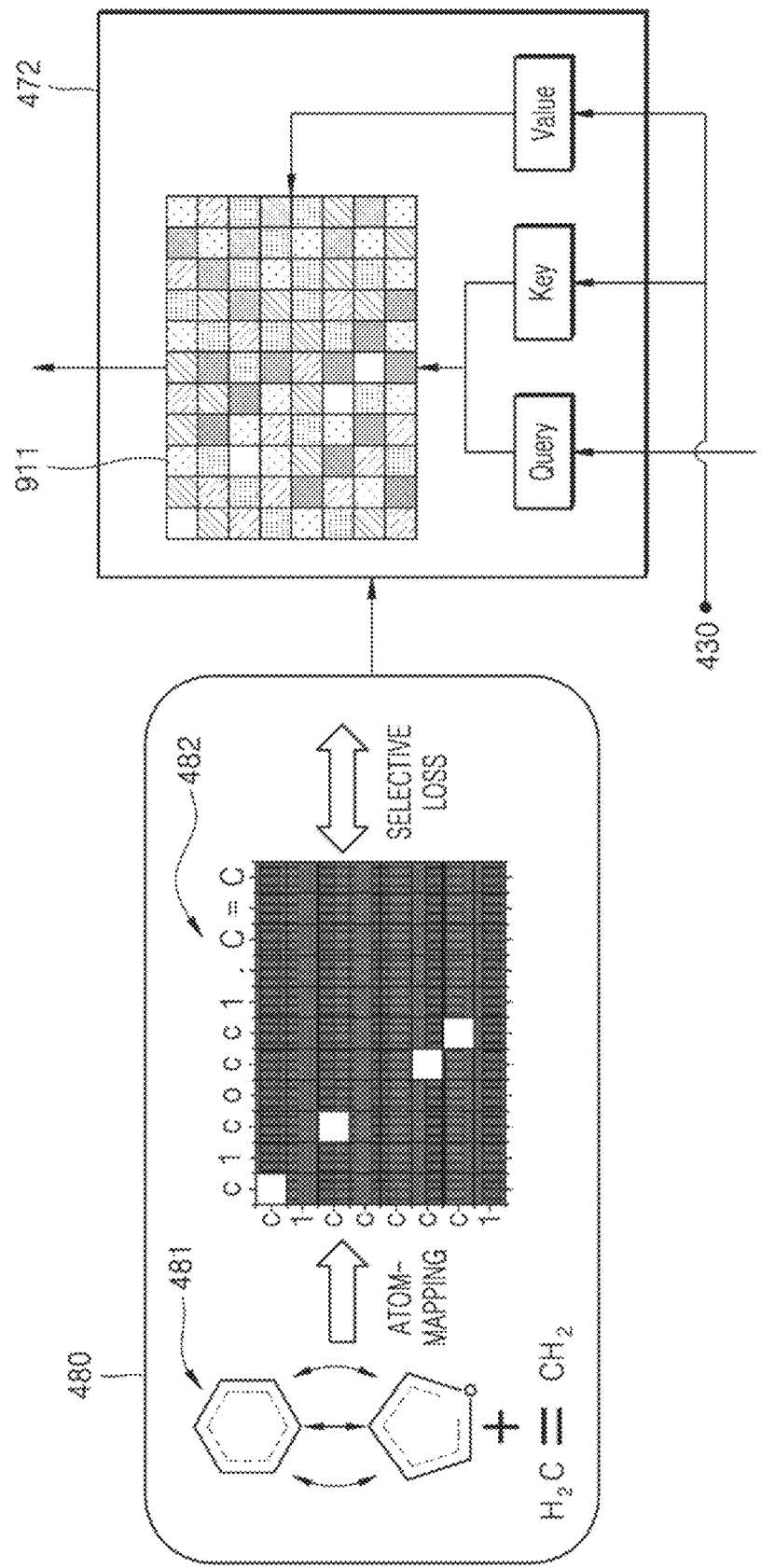
FIG. 9 is a diagram for describing a decoding method according to an embodiment.
Figure 10:
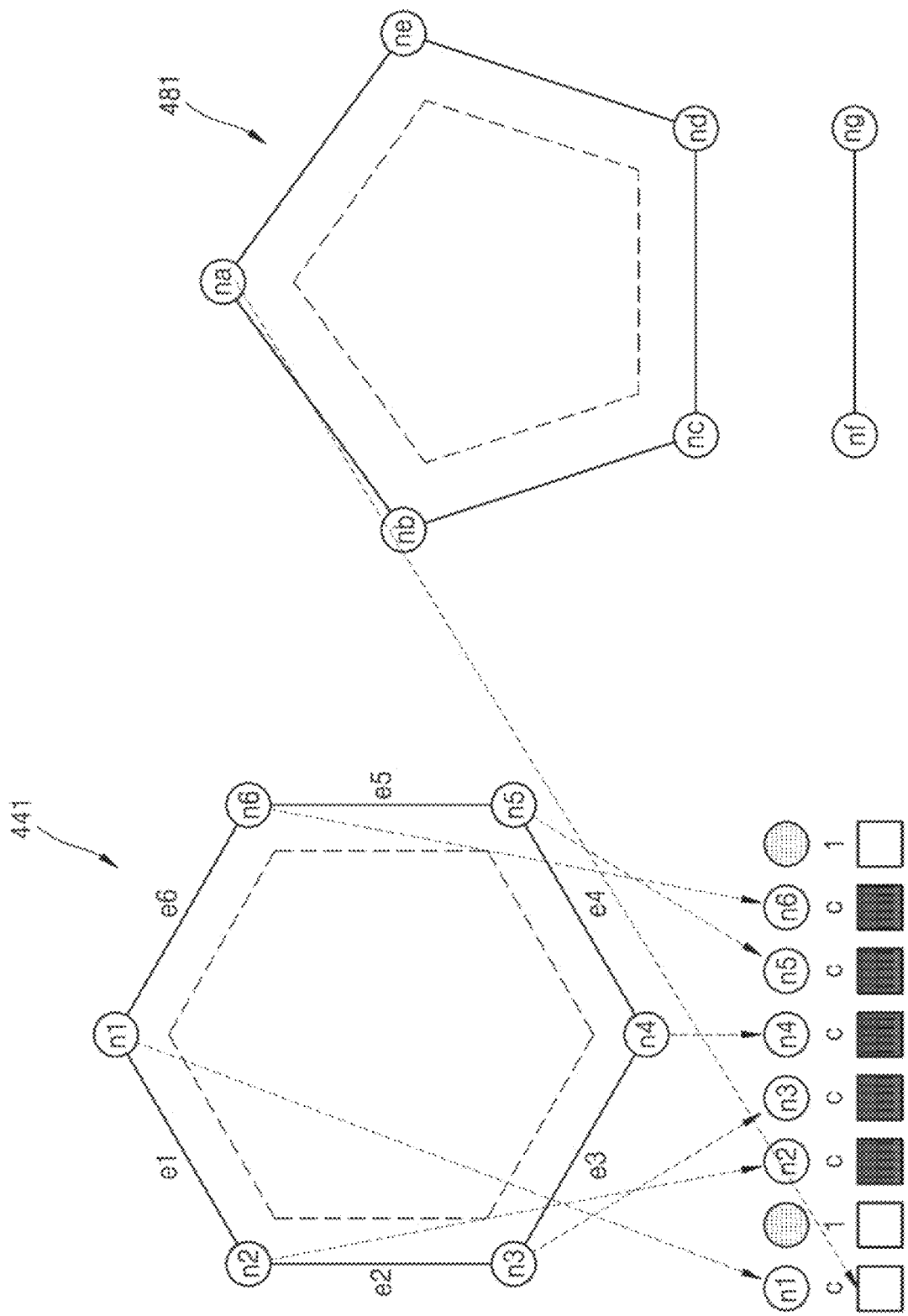
FIG. 10 is a diagram for describing a method of generating a second mask matrix, according to an embodiment.
Figure 11:
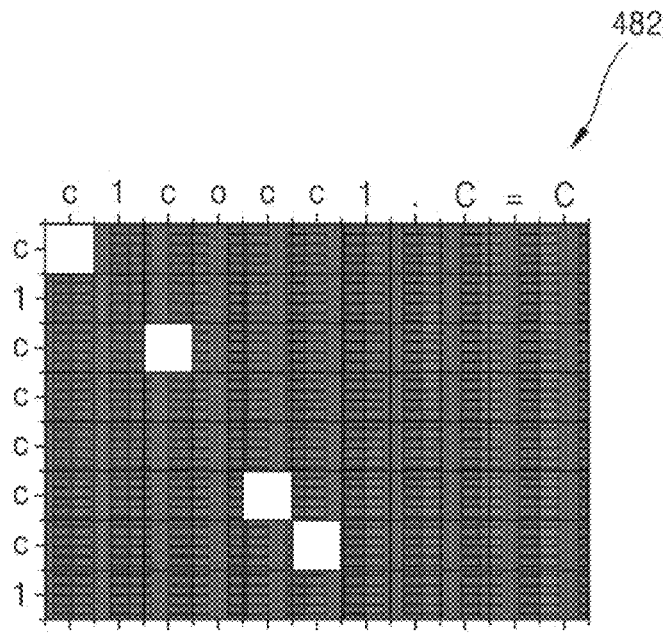
FIG. 11 is a reference diagram for describing a method of generating a second mask matrix, according to an embodiment.

FIG. 9 is a diagram for describing a decoding method according to an embodiment, FIG. 10 is a diagram for describing a method of generating a second mask matrix, according to an embodiment, and FIG. 11 is a reference diagram for describing a method of generating a second mask matrix, according to an embodiment.

Referring to FIG. 9, the decoder cross-attention unit 472 may obtain key and value information from the first character string information 491 provided by the encoder 430. In addition, the decoder cross-attention unit 472 may obtain query information from the second character string information 492. A method of obtaining a query, a key, and a value by the decoder cross-attention unit 472 may be similar to a method of obtaining a query, a key, and a value by the encoder self-attention unit 431. In other words, the decoder cross-attention unit 472 may obtain a query, a key, and a value by multiplying an input vector by a weight matrix.

The decoder cross-attention unit 472 may generate a cross-attention score matrix based on a query and a key. The decoder cross-attention unit 472 may determine a degree of relationship to all keys for each query, and display a result of determination in a cross-attention score matrix. The cross-attention score matrix may include information on a score indicating a degree of relationship between a query and a key. In an embodiment, the cross-attention score matrix may be derived by a scaled dot product attention operation as shown in Equation 1 above.

The decoder cross-attention unit 472 may calculate an attention distribution of the cross-attention score matrix by using a softmax function, and generate an attention value by weighting the calculation result and each value. Attention values may be expressed as a cross-attention matrix 911.

The second mask matrix generator 480 may generate a second mask matrix 482 that masks unnecessary elements from the cross-attention matrix 911.

Because a reaction is not a process of generating a completely new product by completely decomposing a molecule, a molecule of the product and a molecule of the reactant may have a common structure. Accordingly, atom-mapping between the atoms of the product and the atoms of the reactant may be performed. Also, because the cross-attention matrix 911 reflects the relationship between a token of a product and a token of a reactant, an ideal cross-attention matrix 911 catches atom-mapping information. Accordingly, the second mask matrix generator 480 may generate the second mask matrix 482 based on atom-mapping information between a product and a reactant to train the retrosynthesis prediction model by paying attention to the atom-mapping information.

The second mask matrix generator 480 may obtain atom-mapping information from the first graph information 441 and the second graph information 481. The second mask matrix generator 480 may obtain atom-mapping information using a flexible maximum common substructure (FMCS) technique. For example, the FMCS may be an FMCS algorithm implemented in RDkit, but is not limited thereto.

The second mask matrix generator 480 may set any one node from among nodes included in the first graph information 441 as a reference node. In addition, among nodes included in the second graph information 481, a node corresponding to the reference node may be expressed as "1" and the remaining nodes may be expressed as "0".

FIGS. 10 and 11 illustrate a method, performed by the second mask matrix generator 480, of generating the second mask matrix 482 when a product is benzene and a reactant combination is furan and ethylene.

Referring to FIGS. 10 and 11, the second mask matrix generator 480 may set any one of nodes n1 to n6 included in the first graph information 441 as a reference node n1. To distinguish the reference node n1 set by the second mask matrix generator 480 from the reference node set by the first mask matrix generator 440, the reference node set by the first mask matrix generator 440 may be referred to as a first reference node, and the reference node set by the second mask matrix generator 480 may be referred to as a second reference node.

The second mask matrix generator 480 may determine a node na corresponding to the reference node n1 from among nodes na to ng of the second graph information 481. The second mask matrix generator 480 may allocate information about the node na corresponding to the reference node n1 to the second pre-mask matrix. In an embodiment, the second mask matrix generator 480 may allocate "1" to the node na corresponding to the reference node n1 and allocate "0" to the remaining nodes.

In an embodiment, the second mask matrix generator 480 may not mask nodes corresponding to non-atomic tokens as shown in FIG. 10. In other words, the second mask matrix generator 480 may allocate "1" to the nodes corresponding to non-atomic tokens. In another embodiment, as shown in FIG. 11, the second mask matrix generator 480 may mask nodes corresponding to non-atomic tokens to pay attention to the correspondence between atoms. In other words, the second mask matrix generator 480 may allocate "0" to nodes corresponding to non-atomic tokens.

The second mask matrix generator 480 may change the reference node and determine a node corresponding to the changed reference node. Also, the second mask matrix generator 480 may generate the second mask matrix 482 based on the determination result.

When a reactant is R and a product is P, elements included in the second mask matrix 482 may be determined by Equation 5 below.

$$m_{ij} = \begin{cases} 1 & \text{if } R_i, \xleftrightarrow{mapped} P_j, \\ 0 & \text{else} \end{cases}$$

$$m_{ij} = \begin{cases} 1 & \text{if } R_i, \xleftrightarrow{mapped} P_j, \\ 0 & \text{else} \end{cases} \qquad \text{[Equation 5]}$$

In Equation 5, i' may denote the node index of the second graph information 481 corresponding to the $i^{th}$ token of the second character string information 492, and j' may denote a node index of the first graph information 441 corresponding to the $j^{th}$ token of the first character string information 491.

Referring to FIG. 9, the second mask matrix generator 480 may provide the second mask matrix 482 to the decoder cross-attention unit 472.

The decoder cross-attention unit 472 may mask the cross-attention matrix 911 based on the second mask matrix 482.

The role of masking of the decoder cross-attention unit 472 may be different from the role of masking of the encoder self-attention unit 431. This is not only because the atom-mapping is not perfect, but, in the cross-attention, the auto-regressive nature of the decoder 470 generates incomplete character string information (e.g., SMILES) and the decoder 470 may not find atom-mapping information during the generation of a sequence at an inference time. Therefore, the decoder cross-attention unit 472 may allow the cross-attention matrix 911 to gradually train complete atom-mapping by not forcing attention with a hard mask but inducing attention only with information (i.e., $m_{ij}=1$) among incomplete atom-mapping information.

The decoder cross-attention unit 472 may output the cross-attention matrix 911 to which a mask is applied.

The processor 110 may determine elements to be paid attention when calculating an attention loss from the cross-attention matrix 911 to which a mask is applied. The processor 110 may obtain an attention loss of the cross-attention matrix 911 based on elements to be paid attention. The attention loss may denote an error between the second mask matrix 482 and the cross-attention matrix 911. In an embodiment, the attention loss may be determined by Equation 6 below.

$$L_{attn} = \Sigma[(M_{cross} - A_{cross})^2 \odot M_{cross}]$$

$$L_{attn} = \Sigma[(M_{cross} - A_{cross})^2 \odot M_{cross}] \qquad \text{[Equation 6]}$$

In Equation 6, $L_{attn}$ denotes an attention loss, $M_{cross}$ denotes a second mask matrix 482, and $A_{cross}$ denotes a cross-attention matrix 911. In addition, $\odot$ may denote an Hadamard product.

The processor 110 may obtain a cross entropy loss from a second output sequence. In an embodiment, the processor 110 may obtain a cross entropy loss by comparing the second output sequence to the second character string information 492. The method of obtaining the cross entropy loss is not limited to a method.

The processor 110 may calculate a total loss of the retrosynthesis prediction model based on the attention loss and the cross entropy loss. The processor 110 may calculate the total loss of the retrosynthesis prediction model by using Equation 7 below.

$$L_{total} = L_{cs} + \alpha L_{attn}$$

$$L_{total} = L_{cs} + \alpha L_{attn} \qquad \text{[Equation 7]}$$

In Equation 7, $L_{total}$ denotes the total loss of the retrosynthesis prediction model, $L_{attn}$ denotes the attention loss, and α may be an adjustable parameter for balancing the total loss and the attention loss. For example, the parameter may be set to 1, but is not limited thereto.

Because the first mask matrix 442 contributes to the cross entropy loss through the output of the retrosynthesis prediction model, the masking effect of the first mask matrix 442 may be reflected in the cross entropy loss.

The processor 110 may train the retrosynthesis prediction model so that the total loss of the retrosynthesis prediction model is reduced.

As the processor 110 calculates losses of the retrosynthesis prediction model by removing unnecessary elements and paying attention to elements, the efficiency, speed, and accuracy of training of the retrosynthesis prediction model may be improved.

Figure 12:
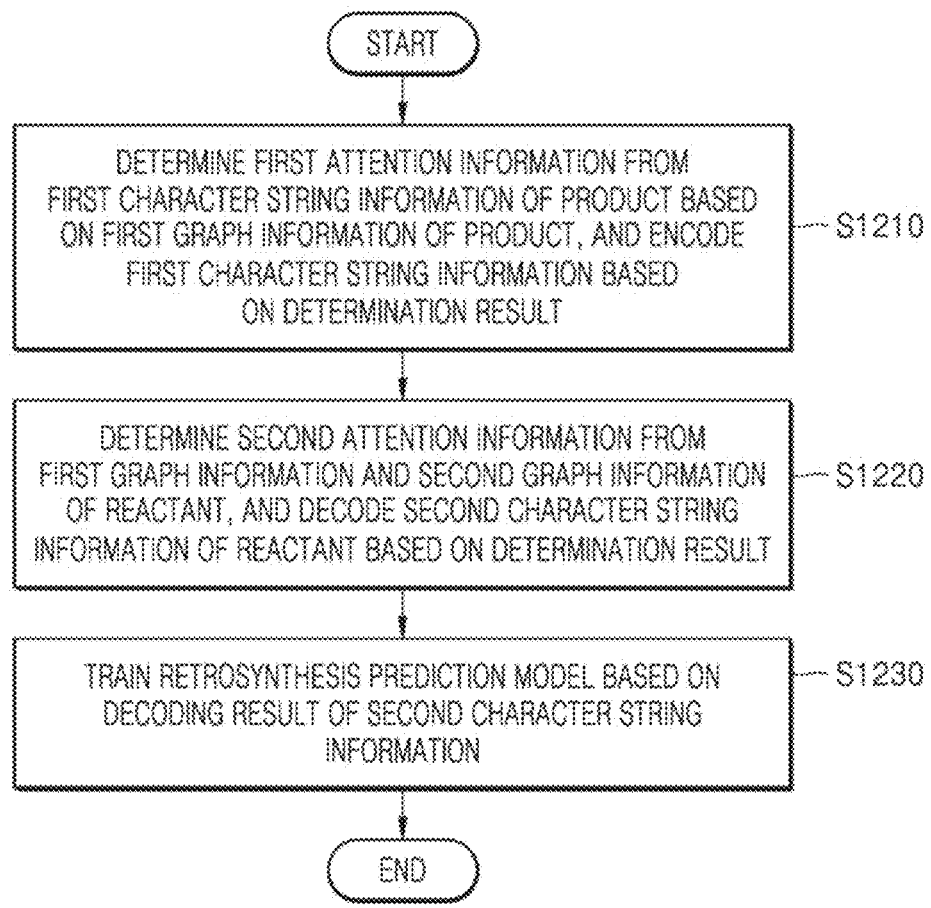
FIG. 12 is a flowchart of a method of operating a retrosynthesis prediction model, according to an embodiment.

FIG. 12 is a flowchart of a method of operating a retrosynthesis prediction model, according to an embodiment.

Referring to FIG. 12, in operation S1210, the processor 110 determines first attention information from the first character string information 491 of a product based on the first graph information 441 of the product, and encodes the first character string information 491 based on the determination result.

Because atoms adjacent to each other are highly chemically related, the first attention information may be information about adjacent atoms that are adjacent to an encoding target atom for efficient training of the retrosynthesis prediction model.

Because atoms adjacent to each other are determined by a distance between nodes in the first graph information 441, the processor 110 may determine information to be paid attention from the first character string information 491 based on the first graph information 441 and a preset reference distance. In this case, the distance may denote a geodetic distance on the graph. Also, the distance may denote a hop neighbor distance on the graph.

The processor 110 may determine neighboring nodes adjacent to each other from the first graph information 441 and encode tokens of the first character string information 491 based on the determination result.

The processor 110 may output the encoded first character string information 491 as a first output sequence.

In operation S1220, the processor 110 determines second attention information from the first graph information 441 and the second graph information 481 of a reactant, and decodes the second character string information 492 of the reactant based on the determination result.

The relationship between a product and a reactant may be represented by a cross-attention matrix, and the ideal cross-attention matrix 911 catches an atom-mapping that represents the relationship between atoms in the product and atoms in the reactant. Accordingly, in order for the efficient training of the retrosynthesis prediction model, information to be paid attention in the first graph information 441 and the second graph information 481 may be atom-mapping information. In this case, the atom-mapping information may be set by using a flexible maximum common substructure (FMCS) technique that utilizes only a pair of 'product atoms-reactant atoms'.

The processor 110 may determine a pair of nodes corresponding to each other from the first graph information 441 and the second graph information 481, and decode tokens of the second character string information 492 based the determination result.

The processor 110 may output the decoded second character string information 492 as a second output sequence.

In operation S1230, the processor 110 may train a retrosynthesis prediction model based on the decoding result of the second character string information 492.

The processor 110 may calculate the attention loss of the cross-attention matrix 911 indicating a degree of relationship between tokens of the second character string information 492 and tokens of the first character string information 491 based on the atom-mapping information. Also, the processor 110 may calculate the cross entropy loss of the retrosynthesis prediction model based on the second output sequence. In addition, the processor 110 may calculate the total loss of the retrosynthesis prediction model by summing the attention loss and the cross entropy loss.

The processor 110 may train the retrosynthesis prediction model based on the total loss. For example, the processor 110 may train the retrosynthesis prediction model until the total loss of the retrosynthesis prediction model is less than a preset reference loss, but is not limited thereto.

Figure 13:
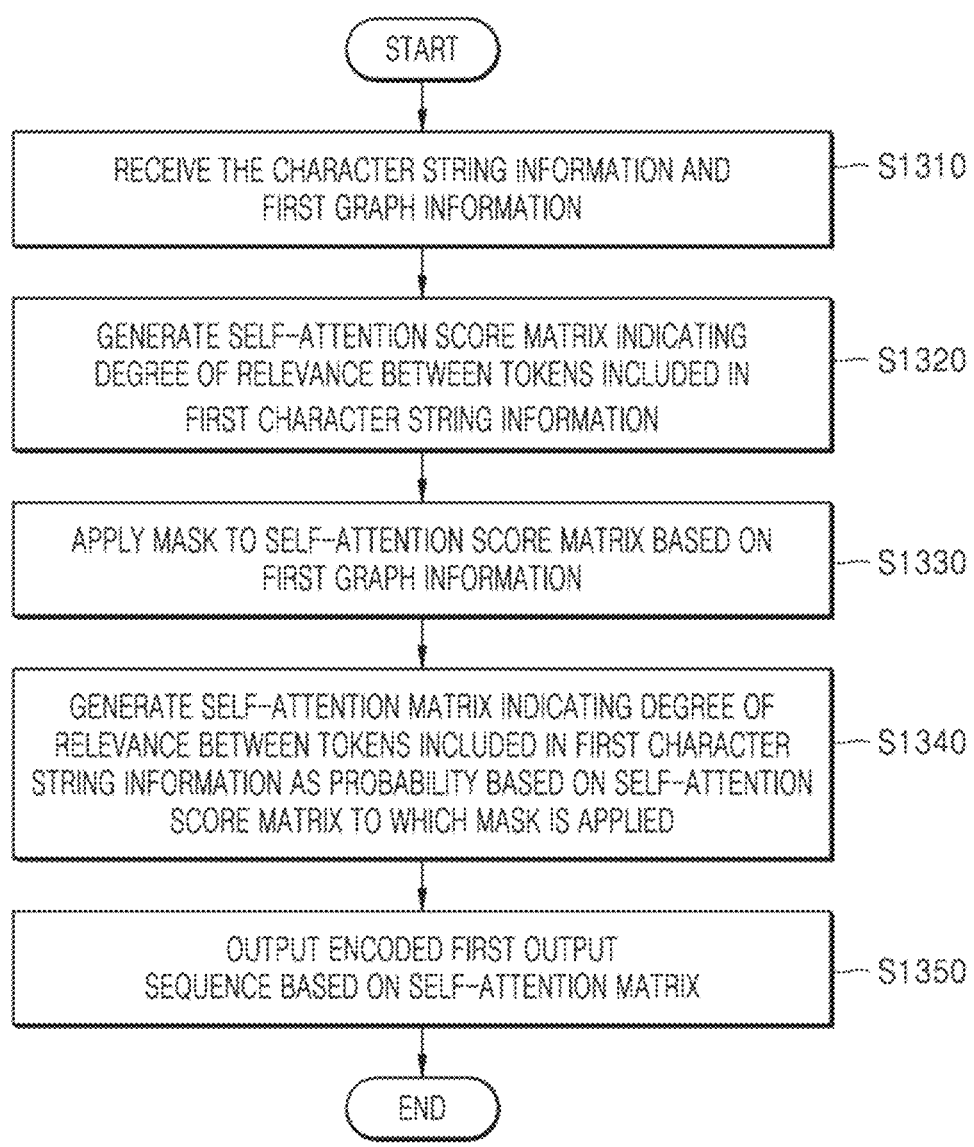
FIG. 13 is a flowchart of an encoding method according to an embodiment.

FIG. 13 is a flowchart of an encoding method according to an embodiment.

Referring to FIG. 13, in operation S1310, the processor 110 may receive the first character string information 491 and the first graph information 441.

The first character string information 491 may be input to the processor 110 in an SMILES format. The first character string information 491 in an SMILES format may include atomic tokens (e.g., B, C, N, and O) and non-atomic tokens, such as the number of cyclic structures having interatomic bonds (e.g., -, =, or #), parentheses, and whitespace.

The first graph information 441 may be input to the processor 110 in a two-dimensional graph format. Graph information may include nodes and edges. A node may include information about an atom of a product, and an edge may include information about a connection relationship between atoms.

In operation S1320, the processor 110 may generate a self-attention score matrix 511 indicating a degree of relevance between tokens included in the first character string information 491.

The processor 110 may obtain query, key, and value information from the first character string information 491 to generate the self-attention score matrix 511.

The processor 110 may determine a degree of relationship to all keys for each query, and display the determination result in the self-attention score matrix 511. The self-attention score matrix 511 may include information about a score indicating the relationship between a query and a key. In an embodiment, the self-attention score matrix 511 may be derived by a scaled dot product attention operation of a query and a key.

In operation S1330, the processor 110 may apply a mask to the self-attention score matrix 511 based on the first graph information 441.

The processor 110 may generate the first mask matrix 442 based on the first graph information 441 and a preset reference distance to mask unnecessary elements in the self-attention score matrix 511.

The processor 110 may generate a first pre-mask matrix by setting tokens included in the first character string information 491 as rows and columns.

The processor 110 may set any one node among the nodes included in the first graph information 441 as a reference node. Also, the processor 110 may determine neighboring nodes existing at a distance from the reference node by a preset reference distance. At this point, the distance may denote a geodesic distance on the graph. Also, the distance may denote a hop neighbor on the graph. The reference distance may be controlled by setting.

The processor 110 may allocate information about a reference node and neighboring nodes adjacent to the reference node to the first pre-mask matrix. In an embodiment, the processor 110 may allocate "1" to the neighboring nodes that are adjacent to the reference node, and allocate "0" to the remaining nodes. In another embodiment, the processor 110 may allocate "1" to the reference node and the neighboring nodes that are adjacent to the reference node and allocate "0" to the remaining nodes.

On the other hand, because the first character string information 491 further includes non-atomic tokens, such as the number of cyclic structures having interatomic bonds (e.g., -, =, or #), parentheses, and whitespace in addition to atomic tokens, tokens of the first character string information 491 and nodes of the first graph information 441 do not coincide with each other. Because these non-atomic tokens may become clear in an entire context of character string information, a wider range of information may be required. Accordingly, the processor 110 may not mask nodes corresponding to non-atomic tokens. In other words, the processor 110 may allocate "1" to nodes corresponding to non-atomic tokens.

The processor 110 may set a different reference distance for each head of the encoder 430 to enhance the training of the retrosynthesis prediction model. For example, the processor 110 may set a reference distance of a first head as a first distance, and may set a second distance different from the first distance to a second head different from the first head.

Based on the first mask matrix 442, the processor 110 may determine elements to be paid attention when encoding the first character string information 491 in the self-attention score matrix 511, and based on the determination result, output the self-attention score matrix 511 to which a mask is applied.

The processor 110 may specify elements having a value of "1" among the elements of the first mask matrix 442. Also, the processor 110 may determine elements of the self-attention score matrix 511 corresponding to the specified elements (e.g., the coordinates are the same). In addition, the processor 110 may not change values of the elements corresponding to the elements specified in the first mask matrix 442 among the elements of the self-attention score matrix 511, but may change the remaining elements to "$-\infty$". Accordingly, the processor 110 may determine elements to be paid attention from among the elements of the self-attention score matrix 511.

In operation S1340, the processor 110 may generate a self-attention matrix indicating a degree of relevance between tokens included in the first character string information 491 as a probability based on the self-attention score matrix 511 to which a mask is applied.

The processor 110 may calculate an attention distribution of the self-attention score matrix 511 to which a mask is applied by using a soft max function, and generate an attention value by weighting the calculation result and each value. The attention value may be expressed as a self-attention matrix. The score of the self-attention score matrix 511 may be expressed as a probability by the soft max function.

In operation S1350, the processor 110 may output an encoded first output sequence based on a self-attention matrix.

Figure 14:
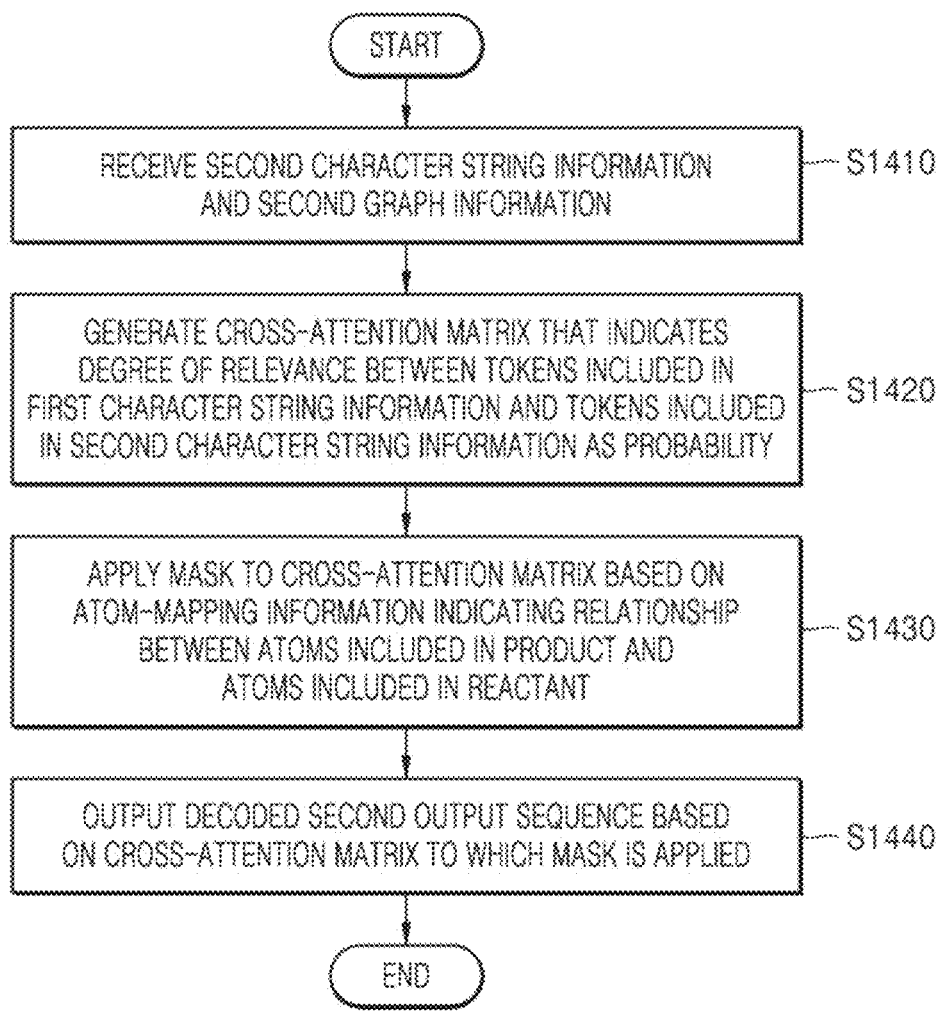
FIG. 14 is a flowchart of a decoding method according to an embodiment.

FIG. 14 is a flowchart of a decoding method according to an embodiment.

Referring to FIG. 14, in operation S1410, the processor 110 may receive the second character string information 492 and second graph information 481.

The second character string information 492 may be input to the processor 110 in an SMILES format. The second character string information 492 in a SMILES format may include atomic tokens (e.g., B, C, N, and O) and non-atomic tokens, such as the number of cyclic structures having interatomic bonds (e.g., -, =, or #), parentheses, and whitespace.

The second graph information 481 may be input to the processor 110 in a two-dimensional graph format. Graph information may include nodes and edges. A node may include information about an atom of a product, and an edge may include information about a connection relationship between atoms.

In operation S1420, the processor 110 may generate a cross-attention matrix 911 that indicates a degree of relevance between tokens included in the first character string information 491 and tokens included in the second character string information 492 as a probability.

The processor 110 may obtain key and value information from the first character string information 491 to generate the cross-attention matrix 911. Also, the processor 110 may obtain query information from the second character string information 492.

The processor 110 may determine a degree of relationship to all keys for each query and display the determination result in a cross-attention score matrix. The cross-attention score matrix may include information about a score indicating a degree of relationship between a query and a key. In one embodiment, the cross-attention score matrix may be derived by a scaled dot product attention operation of a query and a key.

The processor 110 may calculate an attention distribution of the cross-attention score matrix by using a soft max function, and generate an attention value by weighting the calculation result and each value. Attention values may be expressed as a cross-attention matrix 911.

In operation S1430, the processor 110 may apply a mask to the cross-attention matrix 911 based on atom-mapping information indicating a relationship between atoms included in the product and atoms included in the reactant.

The processor 110 may obtain atom-mapping information indicating a relationship between an atom included in a product and an atom included in a reactant based on the first graph information 441 and the second graph information 481.

The processor 110 may obtain atom-mapping information by using an FMCS technique. For example, the FMCS may be an FMCS algorithm implemented in RDkit, but is not limited thereto.

The processor 110 may determine whether atoms included in a product correspond to atoms included in a reactant or not based on atom-mapping information, and may generate a second mask matrix 482 based on the determination result.

The processor 110 may generate a second pre-mask matrix by setting the second character string information 492 as a row and setting the first character string information 491 as a column.

The processor 110 may set any one node among the nodes included in the first graph information 441 as a reference node. Also, the processor 110 may determine a node corresponding to the reference node from among nodes included in the second graph information 481.

The processor 110 may allocate information on about a node corresponding to the reference node to the second free mask matrix. In one embodiment, the processor 110 may allocate "1" to a node corresponding to the reference node and allocate "0" to the remaining nodes.

In one embodiment, the processor 110 may not mask nodes corresponding to non-atomic tokens. In other words, the processor 110 may allocate "1" to nodes corresponding to non-atomic tokens. In another embodiment, the processor 110 may apply a mask to the nodes corresponding to the non-atomic tokens to pay attention to the correspondence between the atoms. In other words, the processor 110 may allocate "0" to nodes corresponding to non-atomic tokens.

The processor 110, based on the second mask matrix 482, may determine elements to be paid attention when calculating an attention loss of the retrosynthesis prediction model in the cross-attention matrix 911, and based on the determination result, output the cross-attention matrix 911 to which a mask is applied.

The processor 110 may specify elements having a value of "1" among the elements of the second mask matrix 482. In addition, the processor 110 may determine that elements of the cross-attention matrix 911 corresponding to the specified elements (e.g., coordinates are the same) are elements to be paid attention when calculating the cross-attention loss of the retrosynthesis prediction model.

In operation S1440, the processor 110 may output a decoded second output sequence based on the cross-attention matrix 911 to which a mask is applied.

Figure 15:
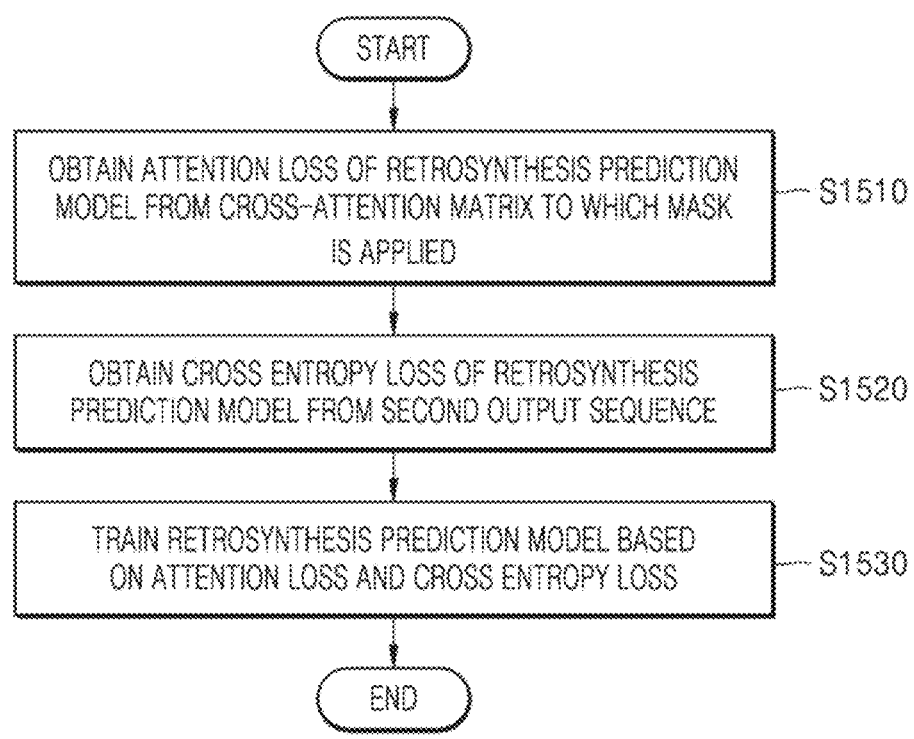
FIG. 15 is a flowchart of a method of training a retrosynthesis prediction model, according to an embodiment.

FIG. 15 is a flowchart of a method of training a retrosynthesis prediction model, according to an embodiment.

Referring to FIG. 15, in operation S1510, the processor 110 may obtain an attention loss of the retrosynthesis prediction model from the cross-attention matrix 911 to which a mask is applied. The attention loss may denote an error between the second mask matrix 482 and the cross-attention matrix 911.

In operation S1520, the processor 110 may obtain a cross entropy loss from the second output sequence. In an embodiment, the processor 110 may obtain a cross entropy loss by comparing the second output sequence to the second character string information 492. The method of obtaining the cross entropy loss is not limited to a method.

In operation S1530, the processor 110 may train a retrosynthesis prediction model based on the attention loss and the cross entropy loss.

The processor 110 may calculate the total loss of the retrosynthesis prediction model by summing the attention loss and the cross entropy loss.

The processor 110 may train the retrosynthesis prediction model so that the total loss of the retrosynthesis prediction model is reduced. For example, the processor 110 may train the retrosynthesis prediction model until the total loss of the retrosynthesis prediction model becomes less than a preset reference loss, but is not limited thereto.

The retrosynthesis prediction method using a template may require domain knowledge of an experienced chemist, however, the neural network apparatus 100 according to the disclosure performs retrosynthesis prediction without a template, thereby increasing time and cost efficiency. Also, the neural network apparatus 100 according to the disclosure may predict combinations of reactants corresponding to a product up to beyond the coverage of the template.

The retrosynthesis prediction method using only the character string information of a compound has low accuracy, and the retrosynthesis prediction method using only the graph information of a compound relies excessively on the atom-mapping information. However, because the neural network apparatus of the disclosure uses the duality of "character string information-graph information", the speed, accuracy, and efficiency of the retrosynthesis prediction model may be increased.

Embodiments of the inventive concept may be implemented as a computer-readable program, and may be realized in computers that execute the program by using non-transitory computer-readable recording media. In addition, the data structures used in the exemplary embodiments described above may be recorded on a non-transitory computer-readable recording medium through various means. The non-transitory computer-readable recording medium includes a storage medium, such as a magnetic storage medium (for example, ROM, floppy disk, hard disk, etc.), and an optical reading medium (for example, CD-ROM, DVD, etc.).

It may be understood that embodiments described herein may be considered in a descriptive sense only and not for purposes of limitation. Descriptions of features or aspects within each embodiment may be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A method of training a retrosynthesis prediction model, the method comprising:
   determining first attention information from first character string information of a product, based on first graph information of the product;
   encoding the first character string information, based on the determined first attention information;
   determining second attention information from the first graph information and second graph information of a reactant;
   decoding second character string information of the reactant, based on the determined second attention information;
   training the retrosynthesis prediction model, based on the decoded second character string information; and
   synthesizing a target product based on a prediction of a combination of reactant molecules for synthesizing the target product, the prediction of the combination of reactant molecules being obtained from the retrosynthesis prediction model.

2. The method of claim 1, wherein the encoding of the first character string information comprises:
   receiving the first character string information and the first graph information;
   generating a self-attention score matrix indicating a degree of relevance between tokens included in the received first character string information;
   applying a mask to the generated self-attention score matrix, based on the received first graph information;
   generating a self-attention matrix indicating a degree of attention of each of the tokens included in the first character string information as a probability, based on the self-attention score matrix to which the mask is applied; and
   outputting an encoded first output sequence, based on the generated self-attention matrix.

3. The method of claim 2, wherein the generating of the self-attention matrix comprises:
   obtaining a query, a key, and a value from the received first character string information; and
   generating the self-attention matrix, based on the obtained query, key, and value.

4. The method of claim 2, wherein the applying of the mask comprises:
   generating a first mask matrix, based on the received first graph information and a preset reference distance;
   determining elements to be paid attention when encoding the first character string information in the self-attention score matrix, based on the generated first mask matrix; and
   applying the mask to the generated self-attention score matrix, based on the determined elements.

5. The method of claim 4, wherein the generating of the first mask matrix comprises:
   setting any one of nodes included in the received first graph information, as a reference node;
   expressing the reference node and adjacent nodes present at a distance separated by the preset reference distance from the reference node, among the nodes, as "1"; and
   expressing remaining nodes, among the nodes, as "0".

6. The method of claim 1, wherein the decoding of the second character string information comprises:
   receiving the second character string information and the second graph information;
   generating a cross-attention matrix indicating a degree of relevance between tokens included in the first character string information and tokens included in received the second character string information as a probability;
   applying a mask to the generated cross-attention matrix, based on atom-mapping information representing a relationship between atoms included in the product and atoms included in the reactant; and
   outputting a decoded second output sequence, based on the cross-attention matrix to which the mask is applied.

7. The method of claim 6, wherein the generating of the cross-attention matrix comprises:
   obtaining a key and a value from the first character string information;
   obtaining a query from the received second character string information; and
   generating the cross-attention matrix, based on the obtained query, key, and value.

8. The method of claim 6, the applying of the mask comprises:
   obtaining the atom-mapping information, based on the first graph information and the received second graph information;
   determining whether the atoms included in the product correspond to the atoms included in the reactant, based on the obtained atom-mapping information, to generate a second mask matrix;
   determining elements to be paid attention when calculating an attention loss of the retrosynthesis prediction model in the generated cross-attention matrix, based on the generated second mask matrix; and
   applying the mask to the generated cross-attention matrix, based on the determined elements.

9. The method of claim 8, wherein the generating of the second mask matrix comprises:
   setting any one of nodes included in the first graph information, as a reference node;

expressing a node corresponding to the reference node, as "1", among nodes included in the second graph information; and representing remaining nodes, among the nodes, as "0".

10. The method of claim 8, wherein the training of the retrosynthesis prediction model comprises:

obtaining the attention loss of the retrosynthesis prediction model, from the cross-attention matrix to which the mask is applied;

obtaining a cross entropy loss of the retrosynthesis prediction model, from the outputted decoded second output sequence; and training the retrosynthesis prediction model, based on the obtained attention loss and the obtained cross entropy loss.

11. The method of claim 10, wherein the attention loss is controllable by parameters.

12. The method of claim 1, wherein the first character string information and the second character string information are in a form of a simplified molecular-input line-entry system (SMILES) code type.

13. The method of claim 1, wherein the first graph information and the second graph information comprise at least one node and at least one edge, the at least one node comprises information of atoms of the product or of the reactant, and the at least one edge comprises information of a connection relationship of the atoms.

14. A non-transitory computer-readable recording medium storing a program for executing the method of claim 1 on a computer.

15. An apparatus for predicting a reaction product by using a retrosynthesis prediction model, the apparatus comprising:

a memory in which at least one program is stored; and a processor that executes the at least one program, to:

determine first attention information from first character string information of a product, based on first graph information of the product;

encode the first character string information, based on the determined first attention information;

determine second attention information from the first graph information and second graph information of a reactant;

decode second character string information of the reactant, based on the determined second attention information;

train the retrosynthesis prediction model, based on the decoded second character string information; and synthesize a target product based on a prediction of a combination of reactant molecules for synthesizing the target product, the prediction of the combination of reactant molecules being obtained from the retrosynthesis prediction model.

* * * * *